US006637649B2

(12) United States Patent
Walsh

(10) Patent No.: US 6,637,649 B2
(45) Date of Patent: Oct. 28, 2003

(54) RECORD AND VERIFICATION METHOD, APPARATUS AND SYSTEM

(76) Inventor: Christopher S. Walsh, 303 Falling Creek Rd., Fredericksburg, VA (US) 22401

(*) Notice: Subject to any disclaimer, the term of this patent is extended or adjusted under 35 U.S.C. 154(b) by 0 days.

(21) Appl. No.: 10/166,167

(22) Filed: Jun. 11, 2002

(65) Prior Publication Data

US 2002/0195488 A1 Dec. 26, 2002

Related U.S. Application Data

(60) Division of application No. 09/833,785, filed on Apr. 13, 2001, which is a continuation-in-part of application No. 09/473,138, filed on Dec. 28, 1999.

(51) Int. Cl.[7] .................................................. G06F 5/00
(52) U.S. Cl. ................... 235/380; 375/454; 375/462.45
(58) Field of Search .............................. 235/380, 375, 235/454, 462.45

(56) References Cited

U.S. PATENT DOCUMENTS

| 4,711,996 | A | * | 12/1987 | Drexler ....................... 235/454 |
| 4,745,268 | A | * | 5/1988 | Drexler ....................... 235/454 |
| 4,857,716 | A | * | 8/1989 | Gombrich et al. .......... 128/903 |
| 5,148,366 | A | * | 9/1992 | Buchanan et al. .......... 364/419 |
| 5,465,082 | A | * | 11/1995 | Chaco ....................... 235/382 |
| 5,482,008 | A | * | 1/1996 | Stafford et al. ............. 119/174 |
| 5,700,998 | A | * | 12/1997 | Palti ........................... 235/375 |
| 5,848,426 | A | * | 12/1998 | Wang et al. ................ 707/505 |
| 5,923,014 | A | * | 7/1999 | Szymusiak et al. ......... 235/375 |
| 5,971,279 | A | * | 10/1999 | Raistrick et al. ........ 235/462.45 |
| 5,979,757 | A | * | 11/1999 | Tracy et al. ................... 186/56 |
| 6,159,013 | A | * | 12/2000 | Parienti ....................... 434/112 |
| 6,192,400 | B1 | * | 2/2001 | Hanson et al. ......... 235/472.01 |
| 6,222,452 | B1 | * | 4/2001 | Ahlstrom et al. ......... 340/568.1 |
| 6,342,839 | B1 | * | 1/2002 | Curkendall et al. .......... 340/5.8 |

FOREIGN PATENT DOCUMENTS

JP          02002123607 A    *    4/2002

* cited by examiner

*Primary Examiner*—Michael G. Lee
*Assistant Examiner*—Allyson Sanders
(74) *Attorney, Agent, or Firm*—Larson & Taylor, PLC

(57) ABSTRACT

A method and apparatus are provided for verification of the identity of a patient undergoing treatment administered by a medical treatment practitioner in a treatment room. An identifying element such as patient chart or patient photograph is provided for the patient which includes a patient identifier, e.g., a barcode, capable of being read by a reader device located within the treatment room. In use, the patient identifier is read by the reader device in the treatment room and a characteristic audio signal, previously assigned to the patient and known to the patient, is generated in response to the reading of the identifying element when there is a match between the patient identifier and a stored identifier for the patient. Treatment of the patient is at least temporarily withheld if any audio signal generated in response to reading of the patient identifier by the reader device is not the characteristic audio signal assigned to the patient. A special patient chart with a removable identifier can be used. A billing method which may involve the scanning step is also provided.

9 Claims, 13 Drawing Sheets

RECORD AND VERIFICATION METHOD, APPARATUS AND SYSTEM

CROSS REFERENCE TO RELATED APPLICATIONS

This application is a Division of U.S. application Ser. No. 09/833,785, filed on Apr. 13, 2001, which is itself a Continuation-In-Part of application Ser. No. 09/473,138 filed on Dec. 28, 1999.

FIELD OF THE INVENTION

The present invention relates to record and verify systems used in medical treatments and, more particularly, to an improved record and verification system for such use which includes a number of important features and advantages as compared with prior art systems including those currently in use.

BACKGROUND OF THE INVENTION

By way of background, it is instructive to briefly consider the history of verify and record systems used in connection with radiation therapy treatment of patients using linear accelerators or other megavoltage radiation units. Verify and record systems were originally designed to verify that radiation treatments were set up correctly by the radiation therapy technologist (RTT). This was accomplished through verification that certain key parameters were within predetermined tolerances. The verify and record process has evolved more recently into an automated set-up procedure that emphasizes rapid through-put, while de-emphasizing verification of treatment parameters that previously were set manually by the RTT. Some record and verify systems currently in use actually take control of the manual process by changing physician-selected field sizes, even though the field sizes fall within selected tolerance limits. The trend toward automated systems has led to reduced interaction between the user and the accelerator which has both positive and negative implications. The philosophy of delivering radiation treatment based on an automated set-up model is grounded in the desire to reduce the potential for human error in the set-up process. The downside of the automated or "black box" approach is the disengagement of the RTT from parameter adjustment, i.e., in relieving the RTT of the task of setting the patient treatment parameters through adjustment of the linear accelerator. The negative aspect of this is that if the RTT does not have to set the parameters manually, the RTT is less conditioned to perform the function manually and, therefore, less conditioned to detect errors when these errors occur, whether these errors are dosimetry programming or process errors and whether these errors occur in manual or automated set-up modes. When the RTT is detached from the procedure of manually setting up the patient for treatment, it becomes more difficult for the overall treatment process to recover should the automated process fail. In this regard, when an RTT sets up a patient manually, the RTT "rehearses" the recovery procedure that would be used if the automated primary process should fail. However, when automated set-ups are employed, the RTT is less "rehearsed" in recovering efficiently when the automated process is not available, because such rehearsal of recovery procedures is not integral to automated treatment delivery. The more safety critical the task, the more the recovery should be rehearsed.

Given current trends in the medical industry, the trend toward automated set-up is irreversible. Further, because of a number of factors including cost pressures, the trend toward staffing reduction is irreversible, at least in the near term. It also appears clear that the electronic record will not totally replace the paper chart, at least not in the near term. In this regard, even if it were proven better for patient care to chart electronically, physician resistance will hinder widespread adoption in the foreseeable future. In general, physicians will not abandon paper charts, either from habit or for medical-legal reasons. Accordingly, the need for maintaining a paper record during implementation of electronic medical record keeping will continue. As a consequence, a further vulnerability of automated radiation treatment systems (in addition to the disengagement of the RTT from the manual recovery process when the automated system is temporarily down), is the potential for mismatches between the electronic record and the paper medical record. These mismatches are commonly due to a failure of the RTT to document treatments in the paper record when the automated system logs the event. The problem of electronic record and paper mismatches is increasing in the specialty of radiation oncology, as reported by clinical medical physicists.

It should be understood that disengagement of the RTT from the manual recovery process increases risk for patient care because the verify and record systems, in many recent configurations, do not check for human error. Record and verify systems, when programmed and executed correctly, can prevent some errors, but not all. Record and verify systems in current use cannot detect human errors when the system itself is the primary process. Additionally, as indicated above, the disengagement of the RTT from linear accelerator parameter adjustment also can disengage the RTT from subtle cues regarding patient identification and radiation field placement. It would be desirable if record and verify systems were configurable to allow automated set-ups at selected times for certain radiation therapy technologists and not for others, such as, for example, when the manual skills of selected RTTs are being assessed. However, the overall trend is clearly toward automated set-up because of the improved throughput which results, as well as the industry-wide momentum toward multi-leaf collimator therapy, which is more optimally performed with automation.

Greater automated throughput can lead to greater risk for other reasons as well. Increased automation means greater potential for a mistake occurring through dose calculation error, with the danger of the error being repeated without prompt detection once the error does occur. The emphasis on throughput also increases the probability of errors in the actual treatment process, characterized by patient identification errors, field sequence errors and field alignment errors. Major preventable ways to harm patients through treatment process failures include (1) treating the wrong patient, i.e., treating a patient with a radiation treatment intended for another patient; (2) treating the right patient, but on a day when the patient is not supposed to receive treatment until other evaluations are performed first (e.g., treating a patient when the patient should have been seen by the doctor prior to the treatment delivery), and (3) treating the right patient but with the improper treatment set-up, i.e., treating with a wedged field without a wedge, treating with the wrong monitor units (MU) programmed into the accelerator, or treating with the wrong energy. In addition, as described above, in the event that the record and verify device should be temporarily unavailable due to a network, or other, problem, there is a distinct possibility or even an increased probability of parameter selection errors due to human error, because the process of automation can change the behavior of the user, making the user more dependent on automation. It is noted that more combination chemotherapy with radiation increases toxicity and therefore increases the potential harm that may occur to a patient if the patient receives the wrong treatment or if the patient is treated without proper evaluation before treatment. Moreover, pushing patients to the limit of tissue tolerance increases the potential for adverse events. Automated treatment may increase the possibility of undetected mistakes related to automated set-up, thereby increasing the possibility of patient injury.

As indicated above, the transition to automated treatment system tends to distract the RTTs for a number of reasons. First, and very basically, the new technology creates a new process. Further, the new process diverts RTTs from traditional cross checks in the treatment room. This is true of systems now in use such as the VARIS, IMPAC and LANTIS systems. In addition, visual distractions are created and the RTTs are diverted from paper chart documentation which can be critical in the safe treatment of a patient.

Although the focus above has been on radiation therapy, it will be appreciated that similar problems exist in other medical treatment settings including chemotherapy as well as in neonatal care, dispensing of medications on both an inpatient and outpatient basis and in other inpatient and outpatient applications wherein patient verification, medication verification, medication delivery device verification and the like are of importance.

SUMMARY OF THE INVENTION

In accordance with the invention, a record and verify method is provided which addresses the issues discussed above. Among other advantages, the method of the invention assists in verification of patient identity, and, according to an important feature, enlists the patient in the identification process. The invention also documents electronically and manually which RTT was responsible for final parameter verification, including documenting the treated patient, and time of cross-check, and thus avoiding electronic record and paper record mismatches. The patient identification component is installed at a workstation and functions even if the system network is down, thereby maintaining an accountability trail as part of the recovery procedure from network failure.

In accordance with a first aspect of the invention, a method is provided for verification of the identification of a patient undergoing radiation treatment administered by a treatment technologist in a treatment room using a radiation source, the method comprising:

providing an identifying card for the patient including an identifying optical code capable of being read by an optical reader located within the treatment room;

causing the identifying card to be read by said optical reader in the treatment room;

generating a characteristic audio signal, previously assigned to the patient and known to the patient and the treatment technologist, in response to the reading of the identifying card when there is a match between the identifying optical code and a stored identifying code for the patient; and at least temporarily withholding treatment of the patient if the patient and technologist do not agree that any audio signal generated is the characteristic audio signal assigned to the patient.

In an advantageous implementation, the identifying card includes a photograph of the patient and the photograph is used by the technologist in identifying the patient.

Preferably, the identification card is affixed to a treatment file containing treatment data for use by the technologist during treatment, and the card affixed to the treatment file is caused to be read by the technologist thereby ensuring that the technologist takes the treatment file into the treatment room.

In a preferred embodiment, the method further comprises generating an electronic record comprising treatment data associated with the treatment to be administered and including said identifying optical code, causing the identifying optical code of the electronic record to be read by a further optical reader in the treatment room, generating said characteristic audio signal in response to reading of said identifying code of the electronic record, and at least temporarily withholding treatment if the patient and the technologist do not agree that any audio signal generated in response to the reading of the identifying code of the electronic record is the characteristic audio signal assigned to the patient. Advantageously, the optical readers are caused to read the respective optical codes of the card and the electronic record at closely spaced times. Advantageously, the respective optical codes are caused to be read by different technologists. In an advantageous embodiment, the optical readers are located on opposite walls of the treatment room. Preferably, the optical readers are each a part of respective verification stations located at different locations inside of the treatment room and the stored identifying code is stored at a verification workstation located outside of the treatment room and linked to the respective verification stations.

More generally, where there is only one optical reader inside the treatment room, the optical reader is preferably part of a first verification station located inside of the treatment room and the stored identifying code is stored at a verification workstation located outside of the treatment room and linked to the verification station inside the treatment room.

In accordance with a further aspect of the invention which combines some of the features discussed above, a method is provided for identification, and verification of the identification, of a patient undergoing radiation treatment by a radiation source administered by a treatment technologist in a treatment room, the method comprising:

providing a treatment file for the patient to be treated containing a prescribed treatment regimen for the patient;

providing an identifying card affixed to the treatment file and including a photograph of the patient together with an identifying optical code capable of being read by an optical reader located within the treatment room;

causing the identifying card of the treatment file to be read by the optical reader in the treatment room;

generating a characteristic audio signal known to the patient and the treatment technologist in response to the reading of the identifying card when there is a match between the identifying optical code and a stored identifying code for the patient; and providing for checking of the treatment file by the technologist if the patient and technologist do not agree that the audio signal generated is the characteristic audio signal assigned to the patient.

As with the method above, the method of this aspect of the invention preferably comprises generating an electronic record comprising treatment data associated with the treatment to be administered and including said identifying optical code, causing the identifying optical code of the electronic record to be read by a further optical reader in the treatment room, generating said characteristic audio signal in response to reading of said identifying code of the electronic record, and checking the treatment file and at least temporarily withholding treatment by the technologist if the patient and the technologist do not agree that any audio signal generated in response to said reading of the identifying code of the electronic record is the characteristic audio signal assigned to the patient. As above, the optical readers are preferably caused to read the respective optical codes of the card and the electronic record at closely spaced times, and, in an advantageous implementation, are caused to be read by different technologists.

As discussed in connection with the first aspect of the invention, the optical readers are preferably located on opposite walls of the treatment room. More generally, the optical readers are each a part of respective verification stations located at different locations inside of the treatment room and, advantageously, the stored identifying code is stored at a verification workstation located outside of the treatment room and linked to the respective verification stations.

In accordance with yet another aspect of the invention, a record and verify method for use with a radiation therapy system including, located in a treatment room, a radiation treatment device for providing radiation treatment and a treatment monitor for monitoring the treatment provided by the treatment device, the method comprising:

using a patient chart for a patient to be treated to enter treatment data into the treatment monitor;

retrieving stored treatment data for use at a verification monitor;

sending the entered treatment data to the verification monitor for comparison with the stored treatment data;

comparing each data entry of the entered treatment data with a corresponding stored data point of the stored treatment data;

using the verification monitor to output an identifier for each data entry which, based on said comparison, is outside of predetermined tolerances;

correcting, as necessary, the data entered into the treatment monitor based on the output received from said verification monitor to produce corrected treatment data;

generating an electronic record of the corrected treatment data;

using a high speed printer to print the prescribed treatment data on a paper verification sheet;

cross-checking the corrected treatment data with previous treatment data;

when the printed paper verification sheet is checked and determined to be accurate, using the radiation treatment device in treating the patient so as to generate actual core treatment data;

printing said actual treatment data on the verification sheet to produce an updated verification sheet;

after completion of a final treatment field of the radiation treatment, reviewing and signing off on the updated verification sheet;

manually entering the actual data obtained from the treatment monitor into the patient's chart and reviewing and signing off on the manual entry of the actual data on the patient's chart; and checking the core treatment data on the printed hard copy against the actual treatment data entered into the patient's chart and, if there is agreement, signing off on the patient's chart and the paper verification sheet.

Preferably, first and second radiation technologists carry out the method, and the first therapist is responsible for steps (a), (c), (f), (j) and (m) and the second therapist is responsible for steps (a), (b), (d), (e), (g), (h), (i), (k), (l) and (n). Advantageously, the first therapist also reviews and signs off on the paper verification sheet upon completion of the method.

In accordance with still a further aspect of the invention, a treatment verification method is provided for use with a radiation therapy system including a radiation treatment device for providing radiation treatment, the method comprising:

providing automated and manual set up options for setting of treatment field values for the radiation treatment device wherein, in the automated option, treatment field values are automatically entered as received from a computer at a verification station and wherein, in the manual option, the treatment field values are entered by a technologist at a radiation treatment device workstation;

setting different predetermined tolerances based on whether the treatment field values are to be entered in an automated manner by the computer in accordance with said automated option or are to be entered manually by the technologist in accordance with said manual option;

selecting between said options and proceeding with the selected option;

comparing each data entry for the entered treatment field values with a corresponding stored data point of stored treatment field values; and using the verification monitor to output an identifier for each data entry which, based on said comparison, is outside of the predetermined tolerances for the option selected.

In accordance with yet another aspect of the invention, a verification system is provided for use in verification of the identity of a patient about to undergo radiation treatment administered to the patient by radiation source in a treatment room under the control of at least one treatment therapist and monitored by a treatment monitor located in the treatment room, said system comprising:

a verification workstation, located outside of the treatment room, including means for storing a patient identifying code for the patient; and at least one verification station linked to said verification workstation and located within the treatment room at spaced locations on opposite sides of the radiation source, said at least one verification station including an optical reader and means for generating an audible output assigned to the patient, responsive to said optical reader reading a patient identifying code assigned to the patient that matches the patient identifying code stored at the verification workstation.

Preferably, first and second verification stations are provided which are located within the treatment room at spaced locations on opposite sides of the radiation source.

In accordance with a further aspect of the invention, a method is provided for verification of the identity of a patient, the method comprising: scanning a patient identifier which identifies the patient to be treated; and generating a characteristic audio signal, previously assigned to the patient, in response to the scanning of the patient identifier when there is a match between the scanned patient identifier and a stored identifier for the patient.

Preferably, the audio signal is known to at least one of (i) the patient and (ii) an authorized caregiver for the patient.

In one implementation wherein the patient is undergoing medical treatment, the method further comprises at least temporarily withholding treatment of the patient if any audio signal generated in response to the scanning of the patient identifier is not the characteristic audio signal assigned to the patient.

In an implementation wherein the patient is a newborn baby, the scanning is carried out to ascertain whether the newborn may properly be removed from its current location. Advantageously, an approved caregiver for the baby is assigned a badge including an identifier and the badge must also be scanned by the caregiver before the baby can properly be removed by the caregiver from said current location. Preferably, the patient identifier is also carried by a name card on the bassinet for the baby. Advantageously, the patient identifier is also carried by an identification band worn by the baby.

In a beneficial implementation of the invention, at least one further identifier, in addition to said patient identifier, is scanned for a match and said characteristic audio signal is generated only after a match is found in each instance that an identifier is scanned. Preferably, the characteristic audio signal is generated only when a match is found in each instance and only when the matches occur in a predetermined sequence.

According to a further aspect of the invention, in addition to said scanning of the patient identifier, a caregiver identifier is scanned to determine whether the caregiver identifier is that of an authorized caregiver for the patient and a check sheet identifier is scanned to determine whether the check sheet is that of the patient, and the characteristic audio signal is generated only after a match is provided in every instance. Advantageously, the characteristic audio signal is generated only when the identifiers are scanned in a predetermined sequence. Preferably, a medication identifier associated with a medication about to be given to the patient is also scanned to determine whether the medication is that intended for the patient and a further, matching characteristic audio signal is generated when there is a match.

According to another embodiment of this aspect of the invention, the patient identifier is carried by a medication container for medication for the patient. Preferably, the patient identifier is also carried by a medication chart on which the physician first writes an order for the medication and both the medication container and the mediation chart are scanned to determine whether said characteristic audio signal is generated in response thereto.

In accordance with yet another embodiment of this aspect of the invention, scanning takes place in a patient dwelling and the patient identifier is carried by a container for a medication which is to be taken by the patient and which is prepared by a pharmacy. Advantageously, a prescription for the medication, including the name of the patient, is initially written by a physician for the patient, the prescription is received by the pharmacy, and the pharmacy determines the corresponding scannable patient identifier assigned to the patient and dispenses the medication in said container carrying said patient identifier.

According to a further embodiment of this aspect of the invention, scanning of said patient identifier comprises scanning of a medical device for delivering a medication to the patient. In one important implementation, the medical device comprises a syringe or a similar medication infusion device.

In accordance with still another embodiment of this aspect of the invention, the patient identifier is carried by a label produced by the caregiver. Preferably, the caregiver initially dispenses a plurality of identical patient identifier carrying labels at the same time. In a preferred implementation, the method is used in chemotherapy treatment of the patient and said labels are applied to container for all drugs used in the chemotherapy treatment, to all syringes used in the chemotherapy treatment and to at least one patient identification member.

Preferably, said scanning of patient identifier comprises scanning of a patient identifying member selected from the group consisting of a patient photograph, a patient treatment chart, a patient identification card and an identification band worn by the patient. In an advantageous application, at least two of the patient identifiers of said group are separately scanned.

Preferably, said scanning is carried out using a scanning device selected from the group consisting of a coded marking scanner, a retinal scanner, a fingerprint scanner, an iris scanner and a scanner for a subcutaneous microchip. In a preferred embodiment, said patient identifier comprises a barcode and scanning of said barcode is carried out using a coded marking scanner comprising a barcode reader.

Advantageously, said characteristic audio signal comprises a non-verbal sound pattern. Preferably, the non-verbal sound pattern comprises a three tone chord. In an advantageous implementation, the duration of said chord is about 2 to 3 seconds.

In another important implementation, the chord is generated at two different times, in close sequence, from two spaced locations and the duration of said chord is about ½ to 2 seconds.

In accordance with another embodiment of this aspect of the invention, scanning of the patient identifier comprises scanning two different identification members carrying the patient identifier and results in the generation of two separate matching characteristic audio signals at two different spaced apart locations in a treatment room when the patient identifiers carried by the two members match said stored patient identifier. Preferably, the two patient identifiers are scanned by two different separate scanning devices spaced apart in the treatment room.

According to yet another aspect of the invention, a method is provided for verification of the identity of a patient undergoing treatment administered by a medical treatment practitioner in a treatment room, the method comprising: providing an identifying element for the patient including a patient identifier capable of being read by a reader device located within the treatment room; causing the patient identifier to be read by said reader device in the treatment room; generating a characteristic audio signal, previously assigned to the patient and known to the patient, in response to the reading of said identifying element when there is a match between the patient identifier and a stored identifier for the patient; and at least temporarily withholding treatment of the patient if any audio signal generated in response to reading of the patient identifier by the reader device is not the characteristic audio signal assigned to the patient.

Preferably, the identifying element comprises an identifying member selected form the group consisting of a patient photograph, a patient treatment chart, a patient treatment verification sheet, a patient identification card and an identification band worn by the patient. Advantageously, the reader device comprises one of a coded marking reader and a fingerprint scanner.

In a preferred embodiment of this aspect of the invention, the first and second reader devices are provided in the treatment room as part of a workstation which also includes first and second spaced audio speakers for generating said characteristic audio signal, and at least a treatment practitioner is required to scan different patient identifying elements each including said patient identifier at the first and second readers, respectively. Advantageously, one of said patient identifying elements comprises a patient chart including a photograph of the patient. Alternatively, or in addition, one of said patient identifying elements comprises a paper patient treatment verification sheet.

In a further embodiment of this aspect of the invention, two medical practitioners carry out the treatment and wherein the treatment that the patient is to undergo includes an automatic setup portion which is carried out automatically under computer control and access to the automatic setup portion is permitted only if both medical practitioners are designated as having automatic setup privilege. According to a related aspect of this embodiment, the method is used in a control system to control, based on preselected criteria, access to an existing automatic download treatment system for a radiation treatment device which automatically transfers prestored patient treatment parameters to the radiation treatment device. Preferably, said criteria include verification of privileges of the medical practitioners responsive to logging by the practitioners onto the control system by effecting scanning of a patient chart by one of the reader devices.

According to a further embodiment of this aspect of the invention, the patient identifier is carried by a container for a medication for the patient and the characteristic audio signal is known both by the patient and the medical treatment practitioner so that both the patient and the practitioner can be assured by hearing the characteristic audio signal that the correct medication container has been provided for the patient. Advantageously, the patient identifier is applied by an in-hospital pharmacy to the medication container and corresponds to a patient identifier previously assigned to that patient during pre-treatment processing.

According to still another aspect of the invention, a patient treatment check sheet is provided containing at least a first field for entry of at least the name of the patient to be treated and a second field including printed patient treatment parameters and blanks to be filled in during the course of treatment of the patient, said check sheet further comprising at least one fixed patient identifier including characteristic coding adapted to be scanned by a scanning device to provide reading thereof and at least one removable patient identifier including said characteristic coding and adapted to be affixed to a further element to be used in the treatment of the patient.

Preferably, the further element to which the removable patient identifier is affixed is the patient identification member selected from the group consisting of a patient photograph, a patient chart, a patient treatment verification sheet, a patient identification card, a patient identification band and a combination of a patient photograph and a patient chart.

In accordance with still another aspect of the invention, a verification system is provided for use in verification of the identify of a patient about to undergo medical treatment administered to the patient in a treatment room under the control of at least one medical practitioner, the system comprising: a verification workstation including electronic storing means for storing a patient identifier assigned to the patient to be treated; at least one scanning device for scanning a scannable patient identifier which uniquely identifies the patient to be treated; and means for generating a characteristic audible output assigned to the patient to be treated and unique to the patient, responsive to matching of the patient identifier scanned by said scanning device and the patient identifier stored by said electronic storing means at said verification workstation. Preferably, the scannable patient identifier comprises a bar code carried by a treatment chart for the patient. Advantageously, the system includes first and second scanning devices, located at spaced locations within said treatment room, for separately scanning scannable patient identifiers carried, respectively, by (i) a treatment chart and (ii) at least one other element associated with the patient to be treated.

In accordance with yet another aspect of the invention, a method is provided for facilitating billing for medical treatment services involving treatment of a patient wherein a patient treatment chart is used in conjunction with the treatment of the patient, the method comprising the steps of: logging onto a computerized billing system when the patient treatment chart is located at a predetermined location in a treatment facility; and generating a billing alert in response to said logging on step so as to ensure patient treatment provided at said location will be billed out. In one important embodiment, the logging on step comprises logging on responsive to use of a scanning device located at said predetermined location to scan a patient identifier on said patient treatment chart.

Further features and advantages of the present invention will be set forth in, or apparent from, the detailed description of preferred embodiments thereof which follows.

DESCRIPTION OF THE PREFERRED EMBODIMENTS

Figure 1:
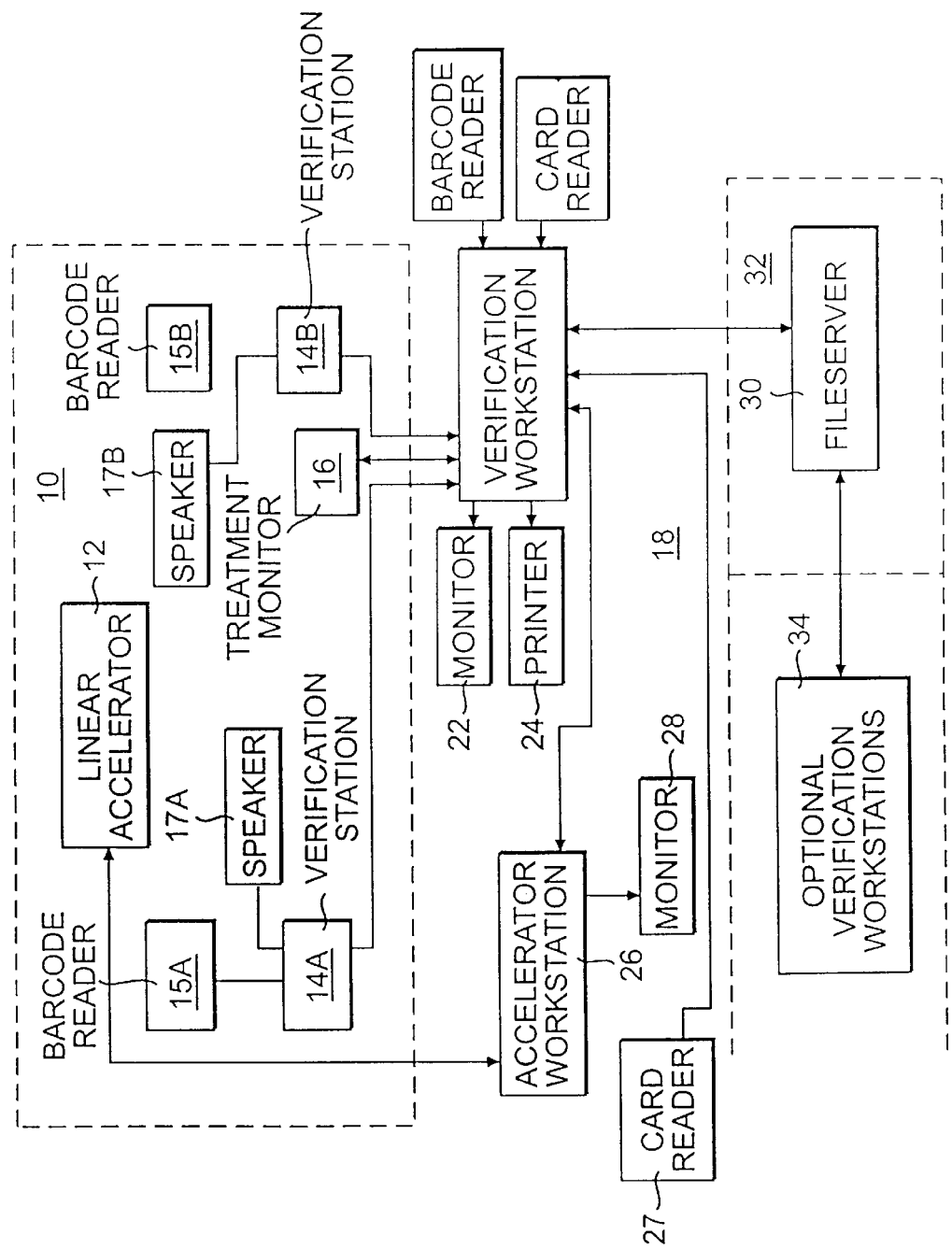
FIG. 1 is a block diagram of a record and verify system in accordance with one preferred embodiment of the invention.

Referring to FIG. 1, a block diagram is provided of one preferred embodiment of the overall system. A treatment room 10 includes a conventional linear accelerator 12 which administers the radiation treatment to the patient and which may be any conventional analog or digital system. Two laser verification stations 14A and 14B are provided in the treatment room 10 along with a treatment monitor 16. The stations 14A and 14B are identical and each preferably includes a respective barcode reader 15A and 15B and a speaker 17A and 17B placed into a single mountable box (not shown). In a preferred embodiment, the verification stations 14A and 14B are located across the treatment room 10 from each other, just beyond the isocenter in the direction of the maze, with the linear accelerator 12 being located between the stations 14A and 14B further, the stations 14A and 14B should be situated so that a first technologist, Technologist A, is able to scan a chart or identification card or photograph not shown) at station 14A on the wall (the left wall is viewed in FIG. 1) while a second technologist, Technologist B, is able to scan a patient's paper verification sheet (as referred to as an electronic sheet, or e-Sheet) at station 14B on the opposite (right) wall. As described below, the e-Sheet is a verification sheet used by the technologist during treatment which shows scheduled and actual treatments. With this setup, each technologist faces towards the gantry of the accelerator 10 and the patient. It is possible to scan the chart on the right rather than the left wall but the e Sheet would then have to be scanned on the left wall scanner. It is understood that while the terms "technologist" or "therapist" are used throughout, the actions described can be carried out by any qualified person including qualified doctors, nurses and other hospital personnel and these terms are intended to cover this.

The treatment monitor 16 is used to display the name of the patient and the treatment field values, i.e., the actual fields which are used by the accelerator 10 and which are verified by the verification system. A typical listing of the treatment fields is provided in Table 1 below.

TABLE 1

Treatment Chart Fields and Descriptions

| Number | Description |
|---|---|
| 1 | Hospital Reference Number |
| 2 | Radiation Oncology Number |
| 3 | Protocol Number |
| 4 | Patient's Date of Birth |
| 5 | Referring Doctor's Name, Address, Phone Number and Identification number |
| 6 | Patient's Name |
| 7 | Patient's Address |
| 8 | Patient's Home Phone Number |
| 9 | Patient's Work Phone Number |
| 10 | Patient's Diagnosis |
| 11 | Diagnosis ICU-9 Code |
| 12 | Palliative or Radical |
| 13 | Definitive |
| 14 | Adjuvant |
| 15 | Pre-Op |
| 16 | Post-Op |
| 17 | Chemotherapy |
| 18 | Series Number |
| 19 | Current Date |
| 20 | Site to be treated |
| 21 | Field Description |
| 22 | Rx Dose |
| 23 | Dose per Fraction |
| 24 | Cumulative Dose |
| 25 | Number of Fractions |
| 26 | Energy |
| 27 | Modify |
| 28 | Reassess |
| 29 | Stop |
| 30 | Planned Rest |
| 31 | Total Treatments Planned |
| 32 | Physician Signature |
| 33 | Previous Radiation Technologist |
| 34 | Consent Signed |
| 35 | Collimator Size |
| 36 | SAD/SSD |

TABLE 1-continued

Treatment Chart Fields and Descriptions

| Number | Description |
|---|---|
| 37 | Gantry Angle |
| 39 | Collimator Angle |
| 40 | Drum/Table Angle |
| 41 | Tray/Wedge |
| 42 | Monitor Units |
| 43 | Comments |
| 44 | Port Film Verifications |
| 45 | Inpatient/Outpatient |
| 46 | Elapsed day count for number of treatments (can start at 0) |
| 47 | Radiation Treatment Technologist |
| 48 | Monitor Units |
| 49 | Tumor Dose Cumulative dosage |
| 50 | Physics |

Located outside of the treatment room in a treatment console area 18 is a verification workstation 20 including a verification monitor 22 (e.g., a standard twenty-one inch color monitor) and an associated high-speed printer 24 connected to the verification workstation 20. Also located in area 18 is an accelerator workstation 26 including a card swipe reader 27 and an accelerator monitor 28. The verification workstation 20 basically comprises a personal computer (e.g., NT 4.0) with a keyboard and mouse, which are not illustrated, together with a barcode reader which is shown separately at 21 and a mounted card swipe reader shown separately at 23. The workstation 20 preferably has a minimum of a 10-Megabyte hard drive and 64 Megabytes of memory.

As indicated in FIG. 1, the system also includes a fileserver 30 for the verification workstation 20 which is normally located in a secured room 32. Preferably, there is a TCP/IP connection from the verification station 20, and the file server 30 has enough memory to support at least one verification workstation. The system may also include further, optional verification workstations 34 for running an administration function described below.

For shorthand purposes, the method of the invention will be referred to hereinbelow as the VEEBAT (Verify Easily Electronically Before and After Treatment) method or process, and the verification workstation 20 will also be referred to as the VEEBAT workstation. Moreover, certain terminology will be used which is explained below and which, for the sake of convenience, is capitalized in the description which follows and also defined in the glossary set forth below.

Before consideration of the process in detail, it is noted that the VEEBAT process may take various paths based on its configuration. For example, the configuration may be set up for each patient daily, or just once. The basic configurable parameters are Treatment Fields, technologist, patient and day of the week. Any combination of parameters may be configured. The VEEBAT verification process may be run at the verification (VEEBAT) workstation 20 in an Auto Setup Mode or Manual Setup Mode. The mode refers to how the Treatment Field Values are entered into the accelerometer (PRIMUS) workstation 26. A Manual Setup will have the Treatment Field Values manually entered at the accelerator workstation 26 and an Auto Setup will have the Field Values automatically downloaded from the VEEBAT workstation 20 which electronically sends the treatment parameters automatically to the Accelerator workstation 26. The VEEBAT process may be configured for Auto or Manual Setup based on four parameters: the technologist, the patient, the current day, and the treatment. The technologist parameter has highest priority, i.e., if a particular technologist is configured for VEEBAT Manual only, then Manual will take precedence over Auto setup.

It is noted that the process is configured for two laser verification stations 14A and 14B in the treatment room 10 but may be overridden to operate with one of the laser verification stations if the other laser verification station fails.

Regarding the VEEBAT workstation 20, the process is configured with the single, above-mentioned barcode reader 21 located at the VEEBAT workstation 20 with the VEEBAT Verification Function. The VEEBAT workstation barcode reader 21 functions only to enable access to the application, not to perform the "echo function" (bar-coded photo/e-sheet cross check) described below.

The process is configured to display various reports at VEEBAT startup. The reports are as follows: partial treatment report, cumulative dose reached report, and scheduled patient report. The reports will be displayed on monitor 22 in a scrolling fashion that can be controlled by the person viewing the reports. The partial treatment report will give a listing of patients who received partial treatment the previous day. This report will include the date and the patient's name. The cumulative dose reached report will list patients who have or will exceed their prescribed cumulative dose. The patient's cumulative doses is prescribed by the Radiation Oncologist. The report will include the date and the patient's name. The scheduled patient report will list all patients who are scheduled for treatment on that date. The report will include the patient's name and time of treatment.

Figure 2:
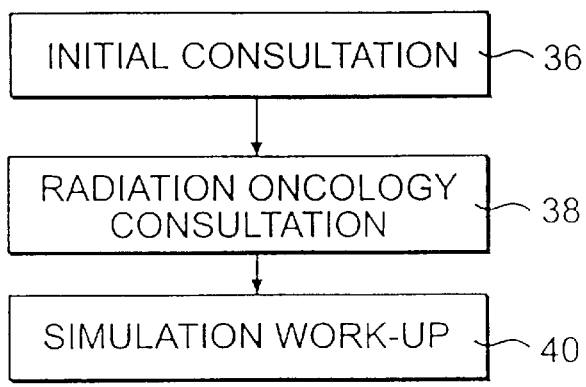
FIG. 2 is a flow chart of an initial consultation sequence involving the patient to be treated.

As an initial matter, referring to FIG. 2, a Patient's File is created on the patient's initial visit. A Patient's File creation consists of the initial consultation and, if advised, the patient's radiation oncology consultation. These steps are indicated in FIG. 2 by blocks 36 and 38. These particular sections of the Patient's File determine if a patient should be treated and, if so, the treatment strategy. A patient's initial consultation determines if radiation therapy is advisable. A radiation secretary creates a Red Folder. The folder contains the patient's referral and medical history. If treatment is advised, a patient is set up for a radiation oncology consultation. Otherwise, the patient's Red Folder will be archived. A radiation oncology consultation determines a patient's prescribed treatment. The patient's initial Red Folder is then moved to a White Folder. The patient's VEEBAT account is created along with a Treatment Folder. The White Folder is a permanent folder for a patient. It will contain the initial Red Folder's contents and radiation oncology consultation.

After completion of a patient's scheduled treatments, all documents in the Treatment Folder are moved to the patient's White Folder. The Treatment Folder is used during the patient's treatments. The folder contains a Treatment Chart, e Sheet, patient set-up photographs and the patient's Polaroid Photo. These items are discussed below. The Treatment Folder also contains the dose calculation work sheets and simulation data, consent form and computer isodose plans, as well as in-vivo dosimetry data. The purpose of using two folders per patient is to reduce conflicts during treatment caused by situations in which radiation treatment technologist (R.T.T.) and nursing personnel simultaneously require access to the medical record. The White Folder and Treatment Folder are presented to the Radiation Oncologist for telephone calls, patient encounters, dictation, and the like. The Treatment Chart contains a patient's original prescription and treatment schedule signed by the Radiation Oncologist. The chart is used during treatment by the Technologist to manually enter Treatment Field Values into the accelerator workstation 26. Typical Treatment Field Values are set forth in Table 2 below.

TABLE 2

| Number | Name |
|---|---|
| 1 | Monitor Units |
| 2 | Jaw/Collimator Size |
| 3 | Collimator Angle |
| 4 | Gantry Angle |
| 5 | Table Drum Angle (optional) |

The e Sheet is, as mentioned above, used during the verification process to store prescribed Treatment field Values. A new Treatment Folder will receive a blank e sheet. A barcode is attached to the e Sheet. A detailed listing of fields and descriptions is provided above. Each Treatment Folder contains patient's set-up photogragh s to indicate the area for treatment along with tattoo markings. Each Treatment Folder also contains a patient's Polaroid Photo. This photograph or picture is used during the verification process to help insure the Treatment Folder belongs with the patient being treated. A barcode is attached to the Polaroid Photo.

The method and system of the invention lends itself well to accounting and billing task. As a first step, the patient's VEEBAT Account is created. The account is used in verification procedure during treatments. The account is generated on a VEEBAT verification workstation 20 (or one of the optional workstations 34) using the VEEBAT Administration Function. A typical chart with a detailed listing of fields and descriptions is provided in Table 3 below. Barcodes on the patient's e Sheet and Polaroid photo will be associated to the patient's VEEBAT Account. As described in more detail below, the patient will be assigned a unique audio signal (e.g., a three tone audio signal in the exemplary embodiment under consideration) that will be used for audio verification by each of the patient, Technologist A and Technologist B in the Treatment Room prior to treatment.

TABLE 3

| Patient Information | |
|---|---|
| RT#: | |
| Patient Name: | |
| Date of Birth: | |
| Referring MD: | (link into UPIN chart) |
| City of Residence: | |
| Telephone No (home): | |
| Telephone No (work): | |
| Diagnosis: | {ascii text} |
| ICD 9 Code: | (link into ICD 9 chart) |
| Chemotherapy | y/n |
| Hormone Therapy | y/n |
| Bar code - Polaroid photo: | |
| Bar code - e Sheet: | |
| (link to actual treatment delivered) | |

A simulation system provides access to a comprehensive library of treatment strategies, including treatment protocols, simulation checklists, guides on how to order tests, and test rationale and, as indicated by block 40 in FIG. 2, a simulation work-up can be provided as part of the initial consultation process.

Turning now to the actual patient treatment process which is one key aspect of the present invention, and referring to FIGS. 3A to 3D, the patient arrives for treatment as indicated by block 42 and checks in with the receptionist. Technologist A obtains the patient's Treatment Folder, scans the patient's Polaroid Photo at the treatment console or workstation 20 to initiate VEEBAT Verification Function, and ensures the patient matches the patient Polaroid Photo, as indicated by block 44. If there is a match, Technologists A and B escort the patient to treatment room 10 (block 46). Technologist B obtains the patient's e Sheet from the Treatment Folder. Technologist A scans the photo at the barcode reader 15A of the verification station 14 (block 48). If Technologist A is unable to scan the photo for any reason, a Supervisor will be requested to help resolve the problem. Once the photo has been successfully scanned, the VEEBAT verification workstation 20 will associate the photo with the patient's VEEBAT Account in the VEEBAT Database (block 50). If the patient's VEEBAT Account is not found, an Audio Error Signal ("beep") will be emitted and a Supervisor will be required to resolve the problem.

Considering in more detail the steps which take place, after Technologists A and B escort the patient into Treatment Room 10, the patient is correctly positioned on treatment table. Technologist A proceeds to either laser verification station 14A or 14B. Technologist B proceeds to other laser verification station. It will be assumed here that Technologist A is at station 14A and Technologist B is at station 14B. Technologist A then scans barcode on the patient's Polaroid Photo at the barcode reader 15A (block 48). The barcode is passed to the VEEBAT Verification Function at the verification workstation 20 to ensure the barcode matches the Polaroid Photo bar code that was just scanned outside the treatment room at the verification workstation 20. If valid, the patient's audio signal is emitted at the verification station 14A. If the Technologist fails to scan the Patient's Polaroid Photo at the VEEBAT verification workstation 20, an Audio Error Signal is issued. This will require the Technologist to go back to the VEEBAT verification workstation 20 to scan the Patient's Polaroid Photo bar code to initiate the VEEBAT Verification Function. Further, if the bar code scanned at barcode reader 15A of verification workstation 14A is a valid VEEBAT account bar code, but does not match the bar code previously scanned at the VEEBAT verification workstation 20, an audio Error Signal will be emitted in this case as well and a Supervisor will be required to resolve the problem. If the patient's e Sheet bar code is scanned first, i.e., if the bar code scanned is the e Sheet bar code associated with the current VEEBAT Account, an audio Warning Signal is issued and the system waits for the Patient's Polaroid Photo bar code to be scanned. If the bar code is not a valid VEEBAT bar code, it will be considered to be a read error. The VEEBAT verification workstation will emit an audio Warning Signal and wait for a re-scan. Considering other potential failures, if the bar code is found but the patient cannot be treated, an audio Error Signal is issued. Again a Supervisor is required to resolve this problem. If the patient's cumulative dose exceeds or will exceed the patient's prescribed dose, a stop order is issued. In this regard, the patient's VEEBAT Account has a stop treatment flag set, which is determined by the Radiation Oncologist.

The patient name and scheduled Treatment Field Values from the selected VEEBAT Account are displayed on the treatment monitor 16 in a large font for easy readability. Also, if a port verification film (PVF) is scheduled, a reminder will appear on the treatment room monitor 16 to remind the technologists. Technologists A and B will visually verify that the name displayed on the monitor matches the patient's name. If not, a Supervisor shall be called to resolve the problem.

Figure 3A:
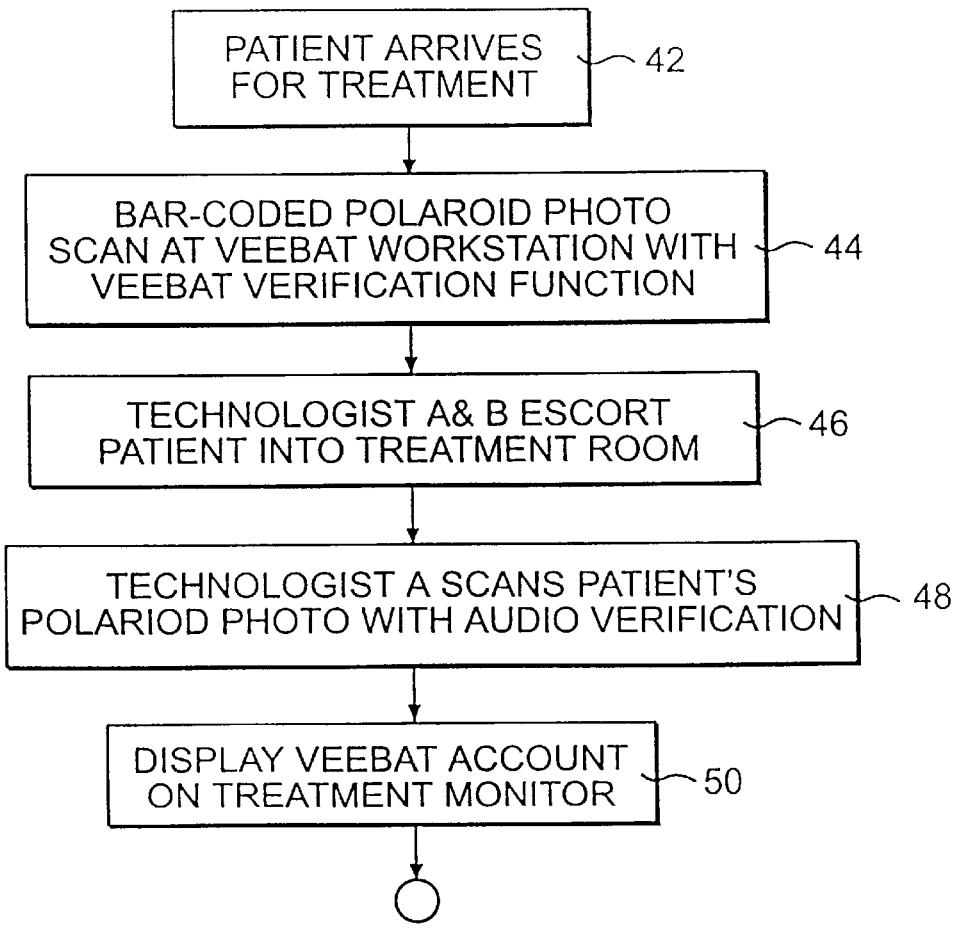
FIGS. 3A, 3B, 3C and 3D, taken together, are a flow chart of a record and verify method in accordance with one preferred embodiment of the invention.
Figure 3B:
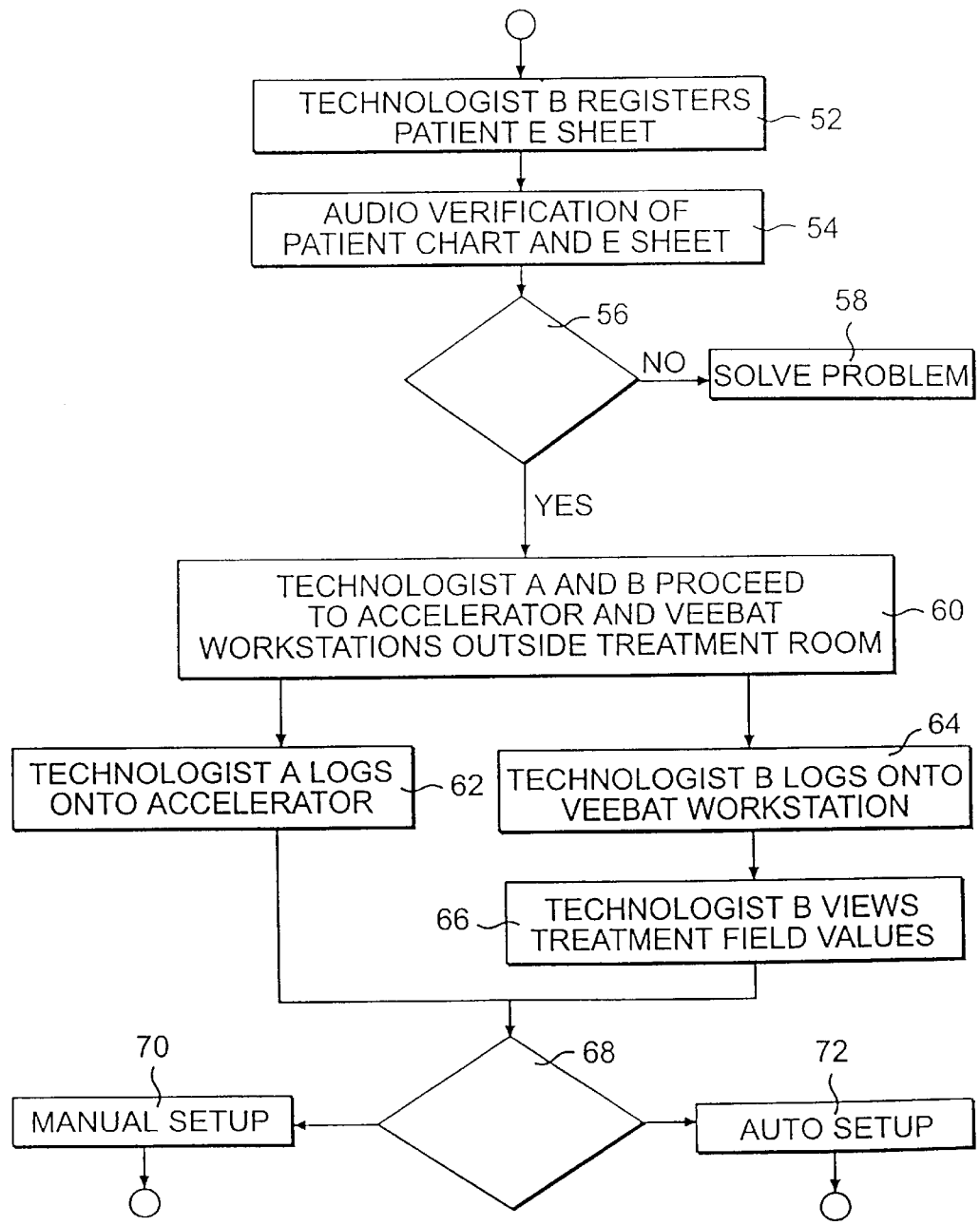

Referring to FIG. 3B, in the next step, Technologist B scans the patient's e Sheet bar code, as indicated by block 52 at barcode reader 15B of verification workstation 14B. The VEEBAT Verification Function then verifies that the bar code is assigned to the patient's VEEBAT Account. Verification of the patient chart and e Sheet is then provided. As shown by decision diamond 56, if valid, i.e., if there is a match, the patient's audio signal is emitted. If there is no match, an audio Error Signal is emitted and a Supervisor is required to resolve this problem (block 58). When the tone is emitted, Technologist A, Technologist B, and the patient all verify that the audio signals emitted from Verification Stations 14A and 14B are the same. The use of identification signals such as unique audio signals is an important aspect of the invention and, among other advantages, provides a comfort level for the patient that is not available with other methods and systems. If anyone questions the comparison of the audio signals, a Supervisor is required to resolve this issue. This aspect of the invention, i.e., the use of an audio signal unique to the patient and the requirement that the patient and the technologist (or technologists) in attendance all verify the signal, is discussed in more detail below.

Next, as shown by block 60, Technologist A proceeds to accelerator workstation 26 and Technologist B proceeds to the VEEBAT verification workstation 20 to access the VEEBAT Verification Function. Technologist A logs onto the accelerator workstation 26 (block 62) and uses the card swipe reader 27 located on the accelerator workstation 26 to register with the Verification Function of the VEEBAT verification workstation 20. If Technologist A is unknown or does not have privilege to apply treatment, then the Verification Function of the verification (VEEBAT) workstation 20 will display a message at the VEEBAT workstation indicating the discrepancy. A Supervisor will be required to resolve this problem.

Technologist B logs onto the VEEBAT verification workstation 20 by using the card swipe reader 23 located on the VEEBAT verification workstation 20 that uses the VEEBAT Verification Function (block 64). If Technologist B is unknown or does not have privilege to apply treatment, then the Verification Function will display a message on the VEEBAT verification workstation 20 indicating the discrepancy. A Supervisor will be required to resolve this problem. Technologist B then views the scheduled Treatment Field Values for the patient at the VEEBAT workstation 20 (block 66).

Figure 3C:
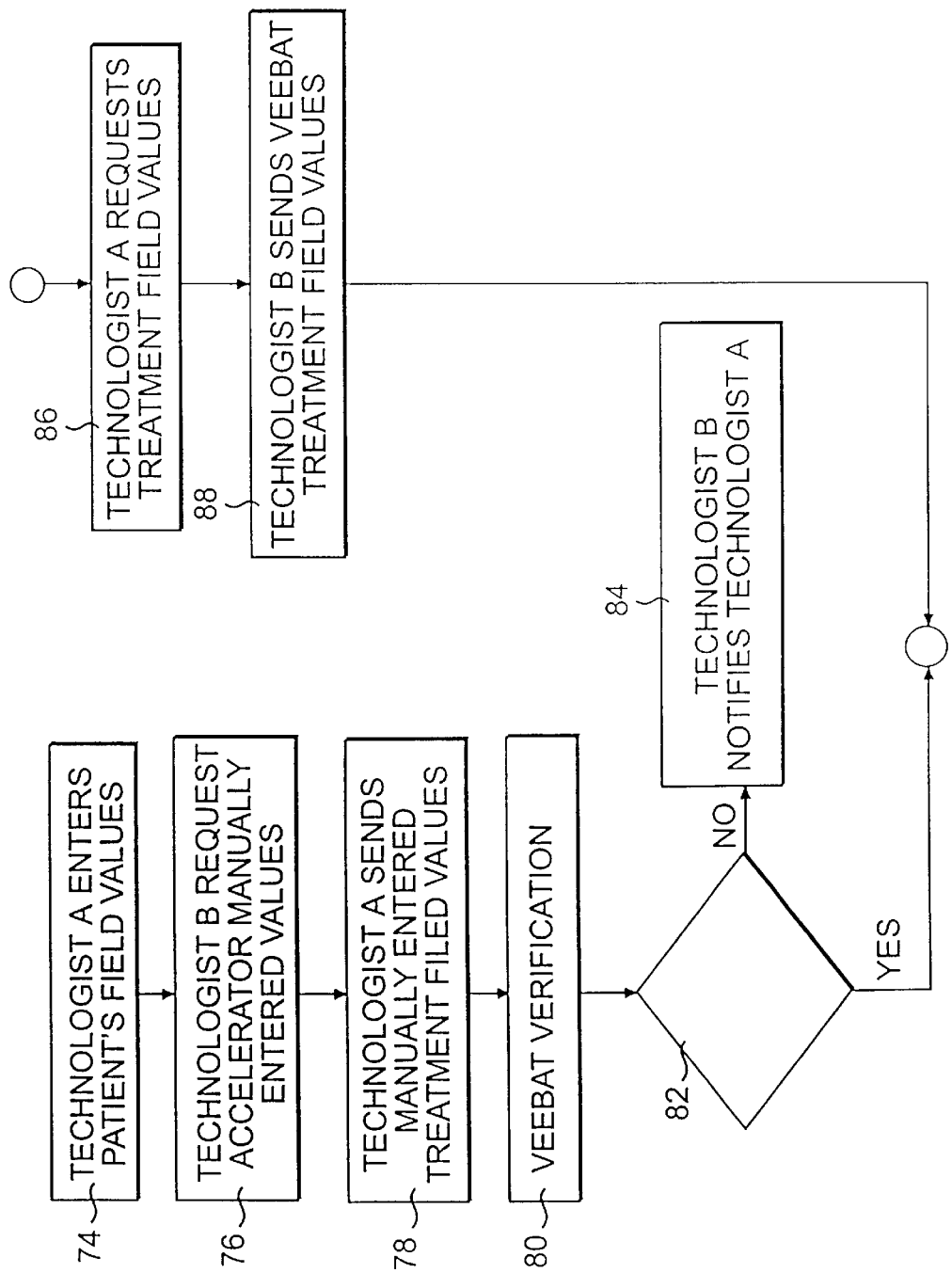

As indicated by decision diamond 68, and was discussed above, the VEEBAT process can be configured for Manual Setup or Auto Setup. If the former confirmation is chosen, as indicated by block 70, the steps set forth at the left side of FIG. 3C are taken. Considering these steps, Manual Setup first requires that Technologist A manually enter Treatment Field Values as indicated on the patient's Treatment Chart at the accelerator workstation 26. The Treatment Field Values are then automatically verified at the VEEBAT workstation 20 by the VEEBAT Verification Function against the patient's prescribed treatment. As shown by block 74, Technologist A manually enters Treatment Field Values indicated on the patient's Treatment Chart at the accelerator workstation 26. Technologist B then places the VEEBAT Verification Function in ready-to-receive mode. Technologist B verbally requests Technologist A to electronically send the patient's Treatment Field Values that were manually entered at the accelerator workstation 26 to the VEEBAT workstation 20 (block 76). The accelerator (PRIMUS) workstation 26 electronically sends the data to the VEEBAT workstation 20 when Technologist A presses a designated button (e.g., the "ACCEPT" button) on the accelerator keyboard (block 78). The VEEBAT workstation Verification Function will only receive values from the accelerator workstation 26 when the VEEBAT verification workstation is in the ready-to-receive mode. At any time, Technologist B has the option to cancel the ready-to-receive mode, thus returning the VEEBAT verification workstation 20 to its previous state.

As indicated by block 80, the VEEBAT Verification Function, after receiving the accelerator values that have been entered, will then verify all patient's Treatment Field Values and confirm that all values are within predetermined tolerances. If any Treatment Field Values are not within the predetermined tolerances, the VEEBAT verification workstation will give an audio Warning Signal ("beep") and display an asterisk beside each field that is not within the predetermined tolerance. If all fields are within predetermined tolerance (i.e., when the output of decision diamond 82 is "yes"), the method or procedure continues as described below.

As indicated by decision diamond 82, if accelerator manual values are incorrect, Technologist B advises Technologist A to reenter any Treatment Field that was flagged at the VEEBAT workstation with an asterisk (block 84). The processing is then repeated. If Technologist A intentionally enters in a value that is not consistent with the predetermined tolerance for any of patient's Treatment Fields, a Supervisor override is required.

Referring to the right side of FIG. 3C, the Auto Setup configuration electronically sends values from the patient's VEEBAT Account through the VEEBAT verification workstation 20 to the Accelerator workstation 26. In this regard, in the specific implementation under consideration, Technologist A places the accelerator workstation in a ready-to-receive mode by depressing a specific key (e.g., the F5 key) on the accelerator keyboard (not shown). Technologist A verbally requests Technologist B to electronically send the patient's Treatment Field Values(block 86). Technologist B, by depressing a download key, sends the requested patient's Treatment Field Values to the accelerator workstation 26.

It is noted that in accordance with a further aspect of the invention different tolerances are provided for Manual Setup and Auto Setup. In Auto Setup, relatively tight tolerances are provided so that, for example, the gantry angle tolerance may be ±1°. Although the automated operation has its advantages, it is important in some circumstances to provide a manual approach wherein the RTT manually sets the Treatment Field Values. Such a manual approach can be customized to the requirements of the patient over time and, in this regard, the Treatment Field Values may be changed over the course of treatment during the day. As a consequence, the tolerances set here should be relatively wider to accommodate the manual approach and, for example, the gantry angle tolerance may set at ±5°. Thus the VEEBAT function provides a different set of tolerances for Manual Setup versus Auto Setup.

Figure 3D:
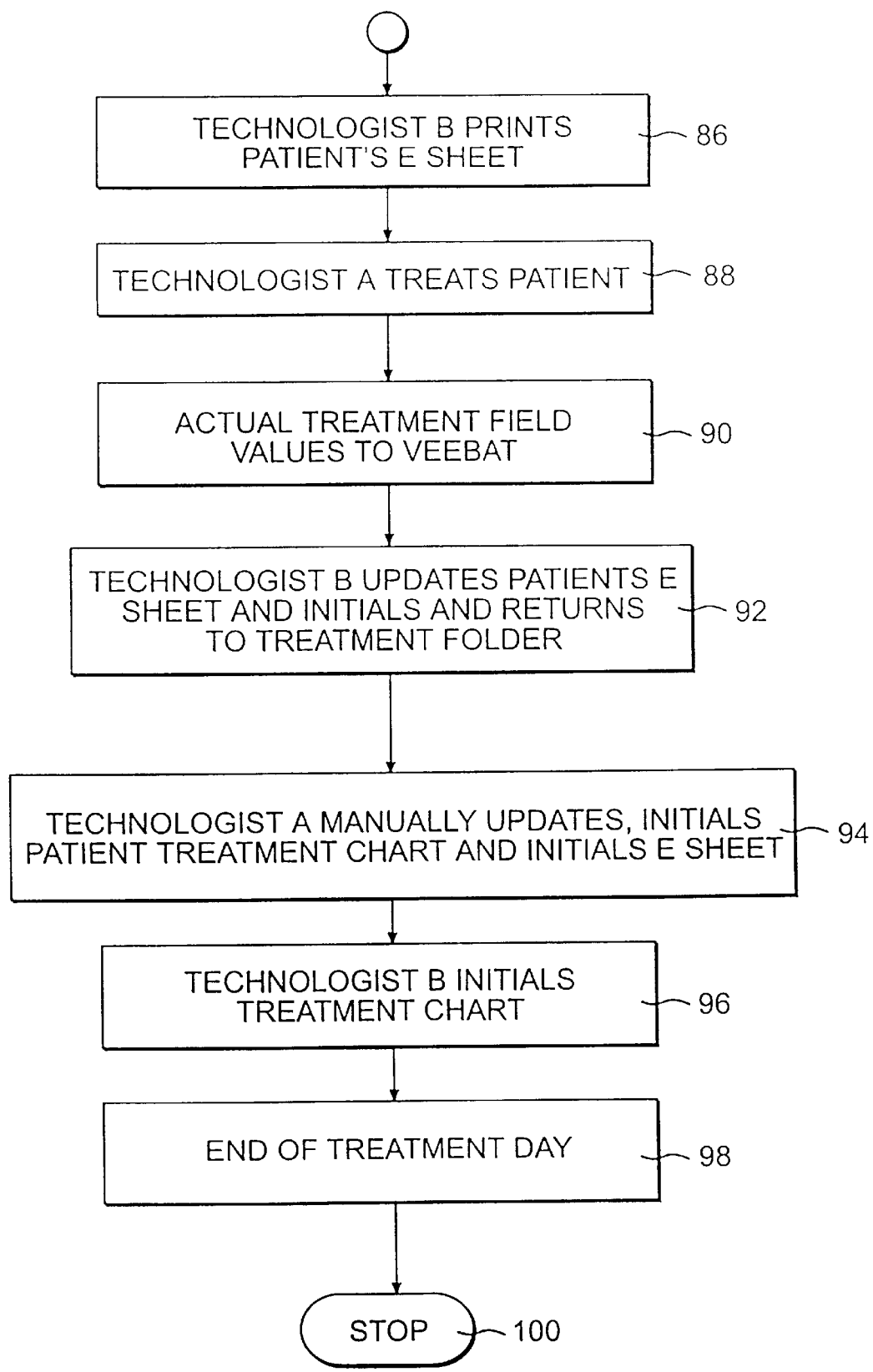

Referring to FIG. 3D, which depicts the remainder of the method or procedure, which is common to both the Manual Setup and Auto Setup, Technologist B requests the VEEBAT verification workstation 20 to print a treatment entry on the patient's e Sheet at printer 24 (block 86), i.e., the date, energy, MU and wedge (i.e., the number of the wedge used, if any) for each prescribed/scheduled Treatment Field of the current treatment session. This occurs before the first treatment field for this treatment session. If this is not the patient's initial treatment session, the technologist will compare the printed values on the e Sheet to the previous treatment values (i.e. the line above on the chart). If the verification fails, a Supervisor is informed of any discrepancies.

As indicated by block 88, Technologist B next gives the Accelerator workstation 26 permission to treat the patient via the VEEBAT verification workstation 20 and verbally informs Technologist A to proceed with treatment. If, during treatment, the accelerator 12 fails to give a complete treatment due to mechanical failure or technologist intervention, Technologist A may "fix" the problem and resume treatment until treatment is complete. However, if Technologist A is unable to complete treatment due to equipment failure or human decision, a Supervisor should, at a later time but prior to next treatment, manually write in the make-up dosage in the right margin of the Treatment Chart and override the patient's VEEBAT Treatment Schedule.

Next, as indicated by block 90, the actual Treatment Field Values are sent to the VEEBAT verification workstation 20 from accelerator workstation 26. The VEEBAT Verification Function updates the screen with actual treatment dose delivered and saves the values to the VEEBAT fileserver 30. If this is not the last treatment beam of the session, the technologists return to the treatment room and set up the patient for the next treatment field. If this is the last treatment, as shown by block 92, Technologist B submits the e Sheet to print the actual monitoring units (MU) on the same row of the e Sheet where the prescribed/scheduled Treatment Field Values are printed on the e Sheet in step 86 above. Thus, in a preferred embodiment, the e Sheet will include columns of entry spaces for the date, energy, wedge and MU, and for initialing by the Technologist or therapist. Such an e Sheet has important advantages because of its simplicity. An asterisk will be printed beside each Treatment Field that received a MU value outside the predetermined tolerance range. If one or more Treatment Field MUs were printed with asterisks, an asterisk will also be printed in the far right-hand column for the day's treatment. This asterisk indicates any discrepancies to the reviewing Physicist. Technologist B should initial the e Sheet at the appropriate session entry space and hand it to technologist A to initial and return to the patient's Treatment Folder (block 92). Technologist A enters the actual Treatment Field Values as shown on the accelerator workstation screen on the Patient's Treatment Chart (block 94). Technologist A then initials the Patient's Treatment Chart at the appropriate session line and hands it to Technologist B. Technologist B initials the Patient's Treatment Chart at the appropriate session line and returns it to the Patient's Treatment Folder (block 96).

Referring to block 98, at the end of the day, various reports can be requested. The reports are generated at a VEEBAT verification workstation 20 using the VEEBAT Administration Function. These reports can include a report of patients who received partial treatment. This report will list each patient that received a smaller dose for that day than was prescribed for that day. This report shall contain patient names and RT numbers.

The reports may also include a list of scheduled patients who were not treated. Such a report will list each patient who was scheduled for treatment that day but did not receive treatment that day for any reason. This report shall also contain the Patient names and RT numbers.

Statistics can also be output for the following treatment types: electron, photon, simple, intermediate and/or complex.

A billing summary can also be produced. This report will list charge codes for each patient treatment as well as patient's name, and concurrent chemotherapy or hormone treatments, if any.

A report can be generated on any information maintained in the VEEBAT database which is located on Fileserver 30.

Considering in more detail the use of a photograph of the patient in generating distinctive audio output, in a preferred embodiment, a photograph of the face of the patient with an identifying barcode is taped or otherwise affixed to the inside front jacket of the Treatment Chart, although the photograph and bar code can take other forms and be printed or mounted on other media. When the chart photograph, with barcode, is scanned by the barcode reader of the corresponding laser verification station in question (station 14A in the example above), a suitable audio output which is uniquely associated with, i.e., specific to, the particular patient is emitted by the speaker (not shown) of the station. Conventional methods are available to generate a specific audio output in response to a corresponding triggering input, including computer generation of sounds or tones. As described above, verification station 14B is used to scan the patient's e sheet. In the specific exemplary embodiment under consideration, the audio output is an audio signal which takes about one second to complete. Of course, while a soothing tone sequence is preferred and has important advantages, other audio outputs can be used including a recording of the patient's name.

In an exemplary embodiment wherein three sequence of tones comprising the three tone chord is determined at simulation by the patient's RT number. For example, departments with different lengths of patient identifying numbers can adjust with a different range of octaves. Four digit departments can use a different octave for the first digit. Five digit departments can use a different octave for the first and second digit. Digits which begin with eight or nine can use sharps or flats as the first digit.

As indicated above, in the specific application under consideration, the second therapist, Therapist B, scans the patient's e Sheet at barcode reader 15B at laser verification station 14B located inside the treatment room on the opposite wall from station 14A, and a confirmatory audio signal emitted from the speaker 17B at station 14B is reassuring the staff that the Treatment Chart's face photo matches the e Sheet. This creates an opportunity to detect whether another patient's e Sheet has been inadvertently placed in the Treatment Chart. The audio signal emitted at station 14A obtained by scanning the patient's Treatment Chart should match precisely the audio signal emitted from the speaker 17B at station 14B. This process of scanning the Treatment Chart, producing a patient specific audio signal and then confirming the audio signal by scanning the e Sheet and producing the audio signal again is referred to herein as "echoing." Echoing is performed most efficiently when the e Sheet is scanned almost immediately after the Treatment Chart is scanned and thus generates its audio signal.

The sequence of Treatment Chart audio signal activation, followed by e Sheet tone activation, confirms that the Treatment Chart photo barcode is the same as the e Sheet barcode. If the wrong Treatment Chart is selected, the patient should notice a non-familiar audio signal, providing a self-managing dimension to the VEEBAT process. Patients often report to their radiation oncology caregivers that they count the seconds of treatment or that they occasionally report perceived changes in the sound of the accelerator as it delivers the radiation treatment. The confirmatory audio signal should reassure anxious patients, while allowing an opportunity for wrong audio signal to be noticed by a patient. This provides an added incentive for the staff to select the correct Treatment Chart since the patient also participates in the cross checking process.

In accordance with a further feature of this aspect of the invention, subsequent fields will be confirmed by a repeat of the last tone and the next tone of the second field, the last tone and the two next tones for the third field, and the last tone and three consecutive tones for the fourth field. Variations of this tone feedback process could be used for three dimensional conformal therapy. Certainly, many patients are already primed for audible feedback and the use of audio confirmation should be of help to patients as well as the staff. The foregoing sequence of barcode scanning brings up the patient's VEEBAT parameters which may then be downloaded for Auto Setup or Manual Setup, followed by verification before and after treatment as described above. This verification process provides a number of important advantages which will now be described.

First, two therapists are encouraged to enter the room with the patient and the Treatment Chart, maximizing the opportunity for satisfactory visual crosscheck. Both therapists are encouraged to enter the room because efficiency inside the room will be rewarded by bringing up the VEEBAT parameters more rapidly, either for Manual Setup verification or Auto Setup. As indicated previously, two therapists are not required to enter the room but if only one therapist enters the room, she or he will still have to bring the Treatment Chart so that no charts will be left on the counter outside the treatment room. Moreover, the lone therapist will still have to set up the patient properly, then activate the VEEBAT queue with the e Sheet at the right wall, i.e., at station 14B, as viewed in FIG. 1.

Further, with two therapists Therapist A must be with the patient at the left side of Accelerator 12 before the audio signal can be generated. The Treatment Monitor 16 and the VEEBAT monitor 22 will display simplified patient parameters only after the e Sheet is properly scanned and the second audio signal is generated at station 14B. Typically, the simplified parameters are defined as a field number, i.e., 1) AP pelvis/prostate, 2) R lat pelvis/prostate, 3) PA pelvis/prostate, and 4) L lat. If Auto Setup has been approved by the Radiation Oncologist for the treatment of the patient, then treatment monitor 16 (in treatment room 10), and VEEBAT monitor 22 (on the treatment counter) will display the simplified patient parameters with, e.g., red letters. If the patient is being treated using Manual Setup, then the corresponding screens will display the simplified patient parameters with different, e.g., white, letters.

Because the display will also appear on VEEBAT monitor 22 at the treatment counter in area 18 which is not in treatment room 10, this provides advanced queuing for treatment, thereby minimizing delays outside the room due to delays in calling up the parameters after the patient's alignment has been visually cross-checked.

In an advantageous implementation, patients are assigned a new RT number and bar code for each course of radiation therapy. In an advantageous implementation, if a patient returns to the radiation oncology department in the future, e.g., for a second course of radiation therapy several years in the future, a fourth note will be added before the three-tone chord assigned for the current year, creating a new four-note chord. This serves as an audible reminder to the staff that the patient has had a previous course of therapy, and that they should watch our for possible overlap of the current field with the prior fields. A third course of therapy will generate a fifth note. In other words, in this implementation, there will be two tones, followed by a pause, followed by the three-tone chord for the current course of radiation treatment. It is more difficult to audibly discriminate longer sequences of tones, and this approach takes advantage of this. The greater the number of prior courses of radiation the patient has had in prior years, the more difficult it is for the therapist to feel comfortable with alpha-beta confirmations, and the more motivated he or she will be to go back to the records to verify lack of overlap with the current fields.

One very important advantage of the verification method and system of the invention is that its primary method of supplemental communication is audio, thereby eliminating the use of additional visual distractions that might divert the attention away of the therapists from the patient's Treatment Chart and actual treatment setup and visual cross-check. This approach also provides for more efficient queuing of the server verification data to the monitor outside the treatment room, so as to provide time for therapists to perform an official verification, followed by treatment, immediately upon reaching the treatment counter or console. Overall, the invention should make treatments faster and more accurate than with existing record and verify systems, because the invention enhances and verifies efficient manual process without altering therapist behavior.

GLOSSARY

| Term | Definition |
| --- | --- |
| Accelerator | The actual accelerator located in the treatment room. |
| Accelerator System | The Accelerator Workstation and the Accelerator. |
| Accelerator Workstation | Part of the Accelerator System, Consists of monitor, special keyboard, and computer. Location is outside the room of the Accelerator. |
| Auto Setup | The Accelerator System receives its Treatment Field Values from the Auto Download Verification Function |
| Bar Code | A label on the Polaroid Photo and e Sheet used to identify electronically the patients VEEBAT Account. |
| Card Swipe | Device used to identify user by badge number |
| Cumulative Dose | Total Radiation received |
| e Sheet | Verification sheet used by Technologist during treatment showing scheduled and actual treatments |
| Error Signal | Audio tone emitted from VEEBAT Workstation when an error requiring a Supervisor is required. |
| ICD-9 Codes | Used to categorize patients cancer location |
| Laser Verification Station A | A verification station located in the treatment room. Consist of a bar code reader and a speaker. Used by Technologist A to read a patients bar coded Patients Chart. |
| Laser Verification Station B | A verification station located in the treatment room consisting of a bar code reader and a speaker. Used by Technologist A in reading a patient's bar coded Patients Chart. |
| Manual Setup | The Accelerator System receives its Treatment Field Values from the Accelerator Workstation |
| MU | The length of a treatment (Monitor Units). |
| Patients File | Patients Treatment Chart, e Sheet, and Polaroid Photo |
| PC | Personal Computer. |
| PVF | Port Verification Film |
| Polaroid Photo | Picture of Patient |
| Radiation Oncologist | Physician |
| Red Folder | A patients folder until treatment is determined |
| RT | Radiation Oncology Number. |
| RTT | Radiation Therapy Technologist |
| RTT | Radiation Therapy Technologist (Technologist) |
| Setup Room | Room where Technologist A and B run the Accelerator and VEEBAT Systems |
| Radiation Oncology Consultation | Work done with the simulator to determine a patients treatment |
| Supervisor | Senior Radiation Technologist |
| TCP/IP | Network communication protocol. |
| Technologist A | Technologist responsible for VEEBAT Verification during treatment. |
| Technologist B | Technologist responsible for Accelerator Workstation during treatment. |
| Total Dose | Total prescribed dose |
| Treatment Field | Actual fields used by the Accelerator and |

-continued

GLOSSARY

| Term | Definition |
| --- | --- |
| Values | verified by the Auto Download Verification Function. See Appendix A for list. |
| Treatment Folder | Folder used by Technologist during treatment |
| Treatment Monitor | A monitor located in the treatment room used to show a patients name and Treatment Field Values |
| VEEBAT Account | Electronic data entered via VEEBAT Workstation with VEEBAT Administration Function. |
| VEEBAT Administration Function | A program running on a VEEBAT Workstation. The program is used to create and access patients VEEBAT accounts stored on the VEEBAT fileserver. The program also provide various report generation functions and administrative functions (i.e. System Backup) |
| VEEBAT Fileserver | A workstation with houses the VEEBAT Database. |
| VEEBAT Process | Verify Easily Electronic Before and After Treatment Process |
| VEEBAT System | The actual components used to implement the VEEBAT Process |
| VEEBAT Verification Function | A program running on a VEEBAT Workstation. The program is used to provide a verification before and after treatment |
| VEEBAT Workstation | A workstation with monitor, keyboard, mouse, CPU, bar code reader, and card swipe. The workstation provides the VEEBAT Administration and/or Verification Function. |
| Warning Signal | Audio tone emitted from VEEBAT Workstation when an error occurred but does not require a Supervisor. |
| White Folder | A patients permanent folder during and after treatment |

Figure 4:
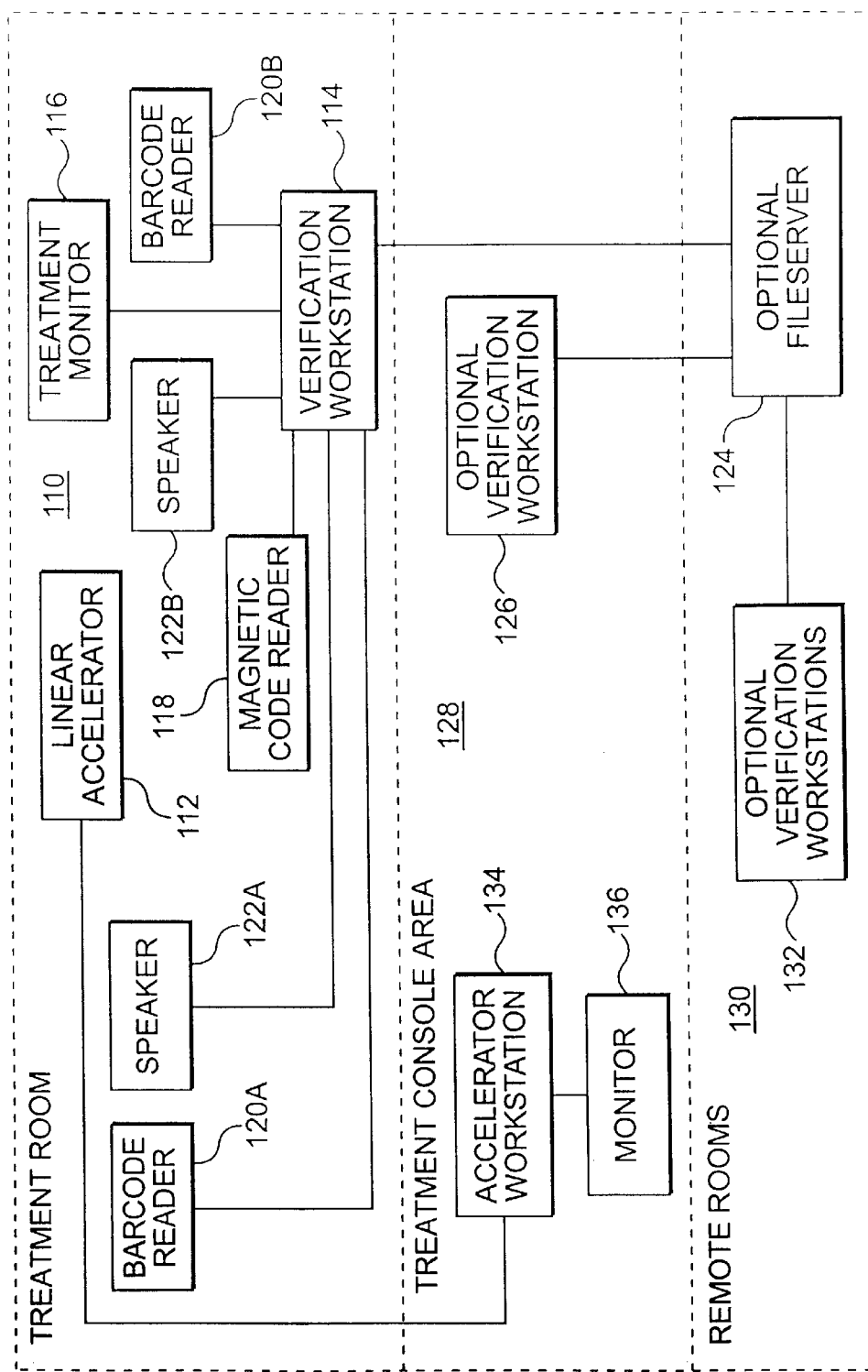
FIG. 4 is a block diagram of a further embodiment of the verification system of the invention as employed in a radiation therapy setting.

Referring to FIG. 4, a block diagram is provided of a further preferred embodiment of the overall system. The system is similar to that of FIG. 1 but incorporates a number of differences as discussed hereinafter or as will become apparent. A treatment room 110 includes a conventional linear accelerator 112 which administers the radiation treatment to the patient and which can be any conventional analog or digital system. A single verification workstation is provided in the treatment room 110 which is comprised of the following components which are not specifically illustrated: a computer processor, a keyboard, and a mouse. The workstation 114 also includes a monitor 116, a single magnetic code reader 118 located at the verification workstation 114, and two sets of barcode readers 120A, 120B and speakers 122A, 122B. In a preferred implementation of this embodiment, each set of barcode reader pairs 120A, 120B and speaker pairs 122A, 122B are located in the treatment room 110 across from each other. In other words, barcode reader 120A and associated speaker 112A are located on one side of the room and barcode reader 120B and associated speaker 122B are located on the other side of the room. An optional fileserver 124 is located in a remote location so as to enable the use of a client-server based system and permitting an optional verification workstation 126 to be located in a treatment console area 128 or other areas or remote rooms 130 as indicated at 132. This enables carrying out of system administration activities, initial patient registration, and report generation but not treatment activities. In the treatment console area 128 are located a conventional accelerator workstation 134 and an associated monitor 136.

With the setup illustrated in FIG. 4, the first technologist, Technologist A, is able to swipe his or her unique ID badge at the magnetic code reader 118 located at the verification workstation 114 inside the treatment room 110, registering the technologist as the "treatment" technologist. The second technologist, Technologist B, is then able to swipe his or her unique ID badge at the magnetic code reader 118, registering the technologist as the "verification" technologist. Technologist A is then able to scan the patient photograph at the barcode reader 120B located near the verification workstation 114. At this time, the system will determine if the "Auto Setup" treatment described above is permitted. Access to the Auto Setup features of the workstation 114 is only allowed if both technologists have privilege for Auto Setup and if Auto Setup is approved for the treatment of the patient. This is determined by the Radiation Oncologist and configured during initial patient registration. Next, the patient is set up at the linear accelerator 112 and oriented properly on the treatment table. Technologist A then scans the patient photograph a second time at the barcode reader 120B, thereby generating the patient unique audio signal. Technologist B then scans the patient's paper verification sheet (referred to above as the electronic sheet, or e-sheet or check sheet) at the opposite barcode reader 120A, thereby again generating the patient unique audio signal.

The verification process described above in connection with FIG. 4 provides a number of important advantages. First, the therapist(s) are required to enter the treatment room with the patient since the only verification workstation permitting treatment set-up, viz., verification workstation 114, is located inside the patient treatment room 110. Having both therapists inside the room maximizes the opportunity for satisfactory visual crosschecks. Second, the patient's chart and photograph must be taken into the room since these items are required to gain access to the verification workstation. Together, these two items are the key to establishing a "default to a safe mode of operation" process or situation. In other words, with the patient's chart in the therapist's hands and the therapist(s) inside the treatment room during the critical patient set-up period, the therapist(s) are given the opportunity to detect their own errors.

Figure 5:
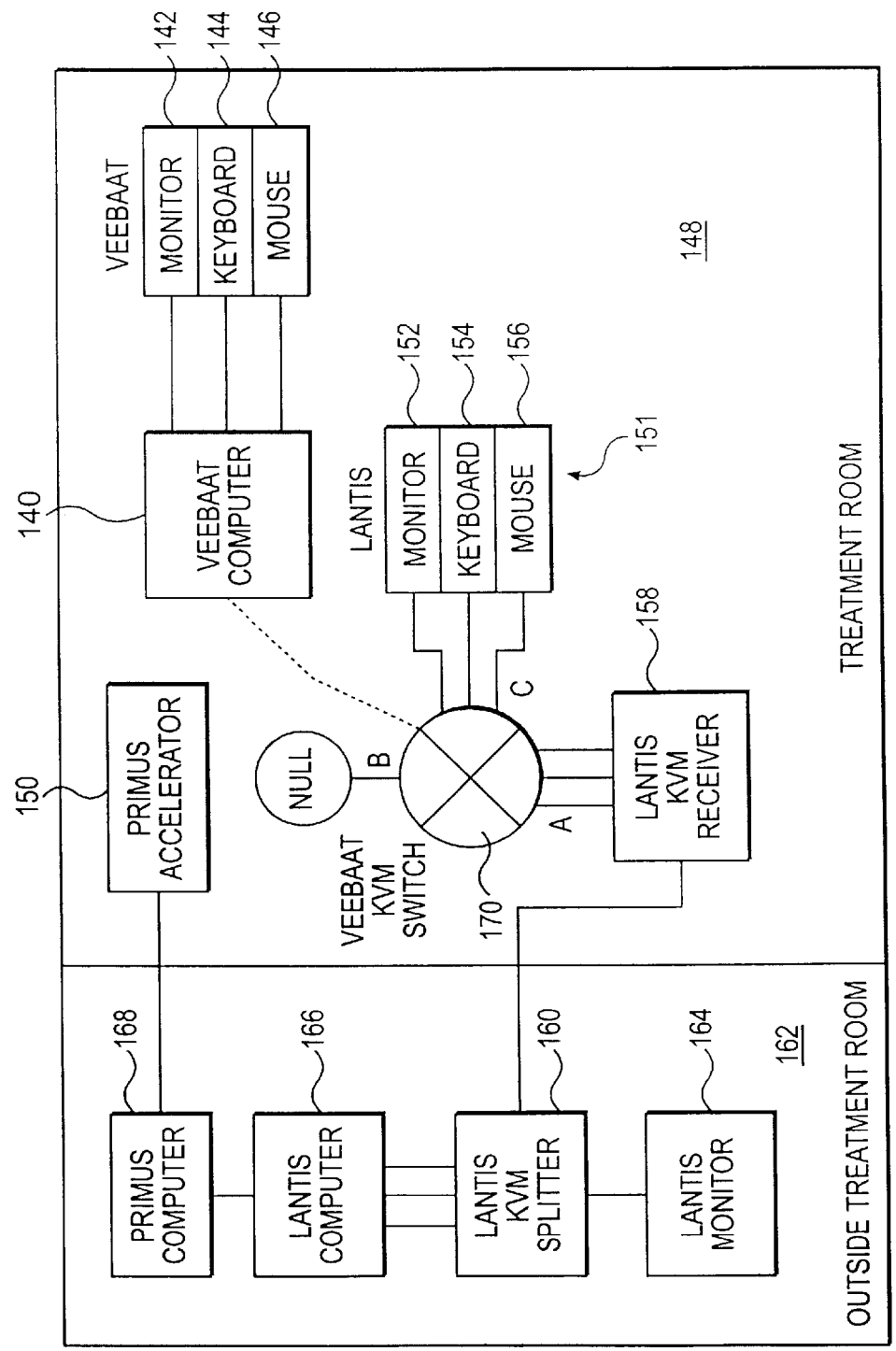
FIG. 5 is a block diagram of yet another embodiment of the verification system of the invention as employed in an access control mode.

In another preferred embodiment, shown in FIG. 5, the system of the invention is utilized with an existing auto-download treatment system (such as LANTIS, IMPAC, or VARIS) in a standard treatment facility. The system of the present invention is indicated in FIG. 2 as the VEEBAAT system, which as indicated above, is the trademark used to identify the system, and includes a computer 140, a monitor 142, a keyboard 144 and a mouse 146. The conventional system includes, in the treatment room 148, a PRIMUS accelerator 150, a LANTIS auto-download unit 181 including a monitor 142, keyboard 154, mouse 156, and LANTIS KVM (keyboard, video, mouse) receiver 158. The latter is connected to a LANTIS KVM splitter 160 which is located in an area 162 outside of treatment room 110 which is, in turn, connected to a LANTIS monitor 164 and to a LANTIS computer 166 connected to a PRIMUS computer 168 which controls accelerator 150. The existing auto-download treatment system communicates with the accelerator's computer to automatically pass patient treatment parameters prestored in a database to the accelerator 150 in the place of requiring these treatments to be entered manually by the technologist.

In the configuration shown in FIG. 5, the system of the invention can be utilized to prevent access to the auto-download system unless a particular set of criteria are met. The criteria are as follows: both technologists must log into the VEEBAAT system, both technologists must have permission to utilize the auto-download system (and as indicated above, this is a configurable item defined within the VEEBAAT program), the ICD-9 code (a code which defines the type/location of the cancer) must be configured to allow auto-download (also a configurable item defined within the VEEBAAT program), and the patient must be configured to allow auto-download (another configurable item with the VEEBAT program). If any of the criteria is not met, access to the existing auto-download system is not allowed. All of the configuration items are controlled within the control system of the invention and can be altered by an administrator who has been given permission to access/alter these settings. The system of the invention also includes a built-in access level security system which enables tailoring authority or permissions for given users of the system. By controlling these configuration items, the treatment facility may limit the use of the auto-download system to individual technologists, individual ICD-9 codes, individual patients, or any combination of the three, as desired.

Access to the auto-download system is controlled by an electronic KVM (Keyboard, Video, Mouse) switch 170 and controlled by computer 140. The KVM switch 170 is located between the auto-download computer 140 and the auto-download unit 151 comprised of monitor 152, keyboard 154 and mouse 156. The computer 140 of the system of the invention controls the switch 170 via an RS-232 serial connection and enables/disables the auto-download system (keyboard/video/mouse) unit 151. The auto-download system is connected to Port A of the switch 170. Port B is left unconnected. When the switch 170 is positioned to Port A, access to the auto-download system is permitted. When the switch is positioned to Port B, access to the auto-download system is prohibited.

The system of the invention allows access to the auto-download system when all the required criteria have been met. If the criteria are not met, access to the auto-download system is prevented, thereby forcing the technologists to treat the patient in manual mode and enter the patient treatment data manually into the computer 168 associated with the accelerator 150. If the criteria are met, access to the auto-download system is permitted and the technologists can then load the patient treatment information from the database and auto-download it to the accelerator computer 168. With this configuration, the auto-download system (i.e., the monitor 152, keyboard 156, and mouse 156) is located inside the treatment room alongside the VEEBAAT system (computer 140 and monitor 142, keyboard 144 and mouse 146). This configuration forces the technologists to enter the treatment room with the patient chart. The technologists are therefore forced into a process which "defaults to a safe mode of operation" should a system failure occur, since the patient chart is required to gain access into the VEEBAAT system and VEEBAAT access is required to gain access to the auto-download system.

In accordance with yet another embodiment of the invention, the invention is used to assist verification of medications to be taken by a patient in a hospital or like patient treatment setting. In this embodiment, a laser barcode scanner or like detector or reader, and an associated speaker, corresponding to those described in connection with previous embodiments, is located near or at the bedside of a patient and preferably mounted on the wall. In addition, software is used which generally corresponds to that described above but which is adapted, and simplified, to carry the functions described.

In use of the system of this embodiment, the physician first writes an order for medication in the patient's chart. The pharmacy within the hospital receives the order for the particular patient and dispenses medication assigned to, i.e., in association with, a patient specific bar code assigned to that patient. In other words, the medication is dispensed in a packet, bottle, carrier, container or the like, with the patient specific barcode thereon.

Next, the bar coded medication is picked up by or delivered to a nurse or other authorized medical practitioner who brings the medication to the patient's beside along with the patient's medication sheet.

In the next step, the nurse scans his or her badge or activates his or her user identifier. Then the nurse provides that the medication sheet is scanned by the scanner or reader, followed by the patient's wristband, and a patient specific tone sequence is emitted based on the barcode on the sheet. The nurse then provides scanning of the medication container or carrier (for example, an I.V. or bar-coded pill dish) so as to generate a matching tone sequence so that the nurse knows that the medication container barcode and medication sheet barcode match. As indicated above, the patient will learn to recognize his or her patient specific tone sequence, i.e., recognize a particular sequence as being uniquely his or hers. Moreover, the nurse will be aware that the patients will learn their specific tone sequence, and thus there is an increased incentive for the nurse to verify that the medication is correct.

When the tone sequence is matched and identified, the patient takes the correct medicine. The system also records and verifies that the correct medicine was given to the patient.

In a further implementation of this particular embodiment, the system is used to assist in identifying authorized personnel assigned to a neonatal nursery and to verify that these personnel are authorized to care for infants, while also creating a verified data record. The only additional equipment to that just described needed is a scanner unit in the newborn nursery.

In this implementation, the identifying audio signal which is specific to the patient (again, preferably a three note chord played in sequence) is assigned to the mother in labor. When the baby is born, the baby is also assigned a unique identifying tone sequence which is generated in response to scanning a barcode carried by the baby's name card on the baby's bassinet. In the case of multiple live births, each baby receives a unique identifying tone sequence. For example, the same chord could be used but with a different suffix or ending (e.g., chord-one, chord-two, chord-three).

The nurse must have a barcode bearing badge and when the nurse takes the newborn from the mother, the nurse's badge is scanned by the nurse through the barcode scanner, followed by scanning of the baby's name card from the bassinet and next followed by scanning the baby's barcode on a wristband or legband, and the baby's three-tone sequence is generated after all of these scanning operations are completed and playing of this sequence confirms that the nurse is authorized to take the baby to the nursery. It is noted in contrast to an alarm or the like, the tone sequence is soothing and reassuring.

When the nurse, baby and bassinet arrive at the nursery, the nurse scans her barcode badge, followed by the bassinet barcode on the bassinet. The corresponding three tones, i.e., the three tone chord, will then be generated, confirming that the assigned nurse for the infant brought the infant into the nursery. The basic program or process verifies and then records in the database the various events that occur and the time at which the events occurred.

When it is time for the nurse to take the baby from the nursery to the mother's room, the nurse scans her bar coded badge through the scanner at the nursery, followed by the baby's name card on the bassinet. Again, the three tones are emitted, indicating that an authorized nurse is taking the infant from the nursery.

In accordance with a further embodiment of the invention, the invention is used to assist verification of medications to be taken by a patient on an outpatient basis. In this embodiment, which is illustrated schematically in FIG. 6, a laser barcode scanner and speaker unit 180 similar to those described above (or an equivalent unit,) are located in the patient's home, indicated at H, and linked to a modem 182 to be monitored by a home health agency or to function with a modem as a "stand-alone" in conjunction with a portable computer 184 such as a personal data assistant (PDA) or a pocket computer. The tone recognition software generally described above would be installed on computer 184 and would be programmed to recognize the barcodes on the patient's medication bottle, packet, pill box or like container or carrier. In an advantageous embodiment, further programming would include a medication scheduler which would provide feedback to the patient about timing of the medication to be taken. For example, the program could provide for emitting the patient's identifying tone when the medication container has not been scanned within a predetermined period (e.g., two hours).

Figure 6:
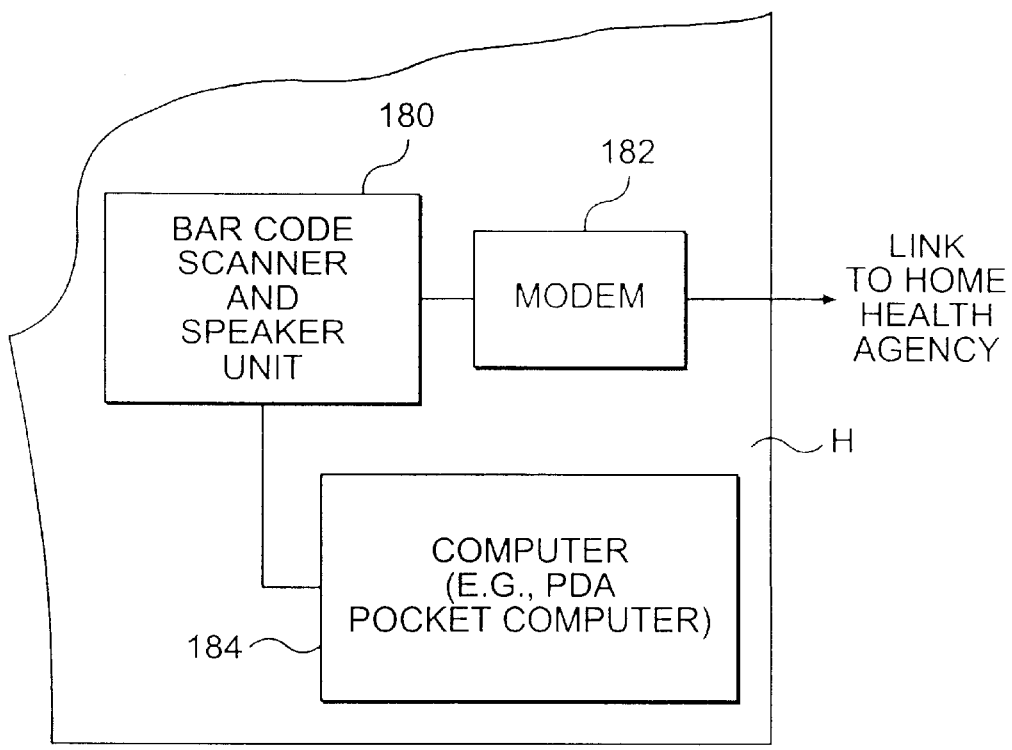
FIG. 6 is a block diagram of a still further embodiment of the verification system of the invention.

In operation, the process would begin with the treating physician writing an order for medication on the patient's prescription. The pharmacy would receive the order for the patient and dispense the medication as assigned to a patient specific barcode on the medication container. The container with the barcode would then be given to the patient. The patient would take the bar-coded medication container to the scanner unit 180 and provide for scanning thereof. A tone sequence or like audio signal, specific to the particular patient as described above, would be emitted thereby indicating that the medication container had not been scanned in the past, e.g., two hours. In an advantageous embodiment, the system would be programmed to provide specific time window guidance as to the taking of the medication, i.e., guidance as to what medication was to be taken and within what time window, with tolerances being programmed in based on input from the pharmacist or health care provider. In any case, the program in computer 184 records and verifies that the medication container was scanned by the patient and records the medication and the time of day for later reporting. If, as shown in FIG. 6, the system is linked by modem 182 to a home health agency, the report can be sent automatically to the responsible parties via a cordless telephone link.

It will be understood that while in the foregoing description, patient photographs and other patient identifiers are used on the source document or card carrying the barcode that is scanned to call up the patient record and/or the audio signal file, other identifiers, which are individualized for a particular patient, can also be employed. Further, while including both a patient photograph and barcode on the patient card has obvious advantages, a single patient identifier can be used, for example, to call up the audio signal file containing the audio signal assigned to the particular patient. Other patient identifiers or identifying processes that can be used for this purpose, and other purposes, include retinal scanning, fingerprint scanning, iris scanning and subcutaneously implanted microchip scanning for individuals who request and consent to such devices for medical care reasons. The patient identifier would be scanned or read by a scanner or reader, preferably located in the treatment room as previously described, so as to trigger the playing of the patient specific audio signal when a patient identification or patient match was established by the scanning operation.

Figure 7:
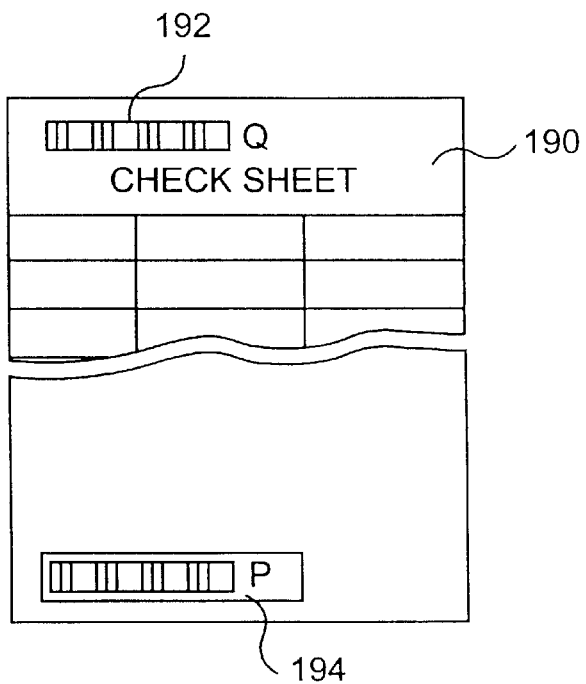
FIG. 7 is a plan view of a check sheet in accordance with a further aspect of the invention.

Turning to yet another aspect of the invention, although a check sheet as described above can be used in the various applications of the invention (after suitable modification to adapt the sheet to the particular application), in accordance with this further aspect of the invention, an improved check sheet is provided which is shown schematically in FIG. 7 and is generally denoted 190. As shown, the check sheet 190 has a first barcode 192 at the top middle portion of the check sheet, and a second barcode 194 at the lower left portion of the check sheet. As discussed above, a check sheet functions in radiation therapy as a manual quality assurance tool in real-time. In the illustrated embodiment, the barcode 192 is fixed to the top of the page and contains the patient's radiation therapy (RT) number with a Q suffix. In contrast, the barcode 194 is removably affixed, e.g., by an adhesive, is located at the lower left corner of the check sheet 190 and contains the patient's RT number with a P suffix. Barcode 194 can be peeled from the check sheet and applied to, i.e., stuck on, the patient's identification photo, chart, identification card or identification band at the time of simulation (e.g., virtual, fluoroscopic, clinical).

When the applied stick-on barcode 194 (photo, chart, I.D. card or patient band) is scanned, the patient's personal audio signal file is activated, i.e., made audible. As indicated previously, in a preferred embodiment, the audio signal is known and recognized by the patient and the radiation therapy technologists (R.T.T.s) or other medical practitioner or caregiver. Scanning the fixed barcode 192 at the top of the check sheet 190 generates the same audio signal, confirming that the stick-on barcode 194 matches the fixed barcode 192 at the top of the check sheet 190. The check sheet 190 can be used in in-patient medication delivery and infant identification such as those described hereinabove, with I.D. bands, cards, badges and medication check sheet verification. The check sheet 190 can also be used in the outpatient medication compliance system discussed previously.

The check sheet 190 minimizes the potential for mismatched barcodes because it can be assured that the patient's number is the same on both barcodes 192 and 194. Use of check sheet 190 is a one-step procedure which optimizes the probability of correctly applying the peeled barcode label to the correct patient record. The check sheet serves as an additional safety net in the event other verification systems are inoperative.

Figure 8:
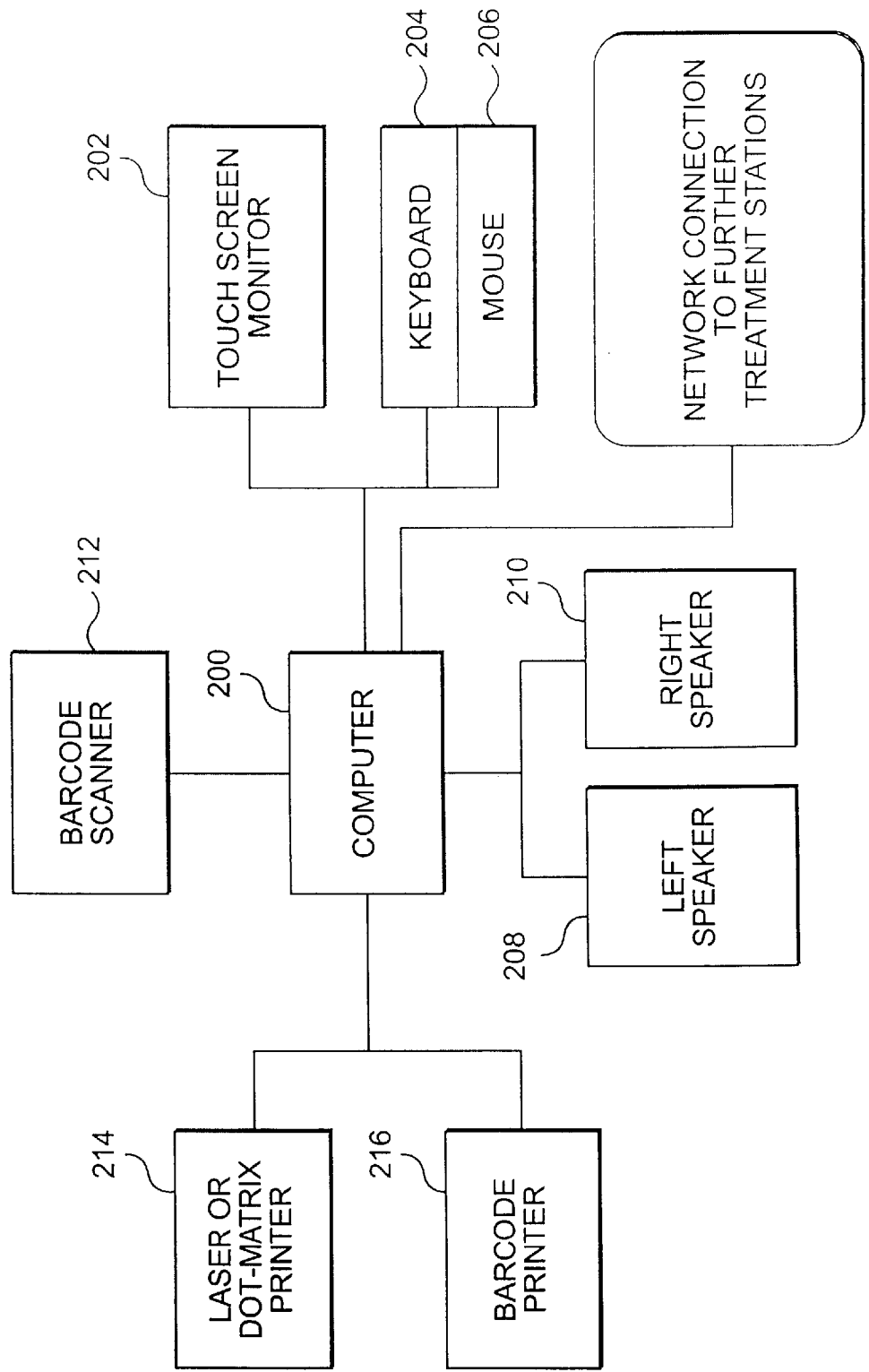
FIG. 8 is a block diagram of a treatment station in accordance with yet another embodiment of the invention.

The invention has principally been described above with respect to the application therefor to radiation therapy and although other applications have also been described, there are still other applications of importance. One of these is in the field of chemotherapy. The system used for this application would include anywhere from one to many individual stations. The hardware used in a typical station of such a system is shown in FIG. 8 and is comprised of a computer 200, a touch-screen monitor 202, a keyboard 204, a mouse 206, two speakers 208 and 210, a barcode scanner 212, a laser or dot-matrix printer 214, and a barcode printer 216. In an advantageous implementation, all of this equipment is located on a single computer stand (not shown). The laser/dot-matrix printer 214 is used for printing of reports generated by the computer program. The barcode printer 216 is used in printing of barcode labels for new patients to be treated.

Referring to FIGS. 9(a) to 9(d), there are shown the basic steps in a preferred embodiment of the treatment verification and record method of this aspect of the invention. However, before considering FIGS. 9(a) to 9(d), it will be understood that when a new patient is to receive chemotherapy, the process begins with assembly of a new patient chart. The steps involved are as follows:

Patient information (name, ICD-9 diagnosis, and so on, as required) is entered into the computer 200 for the new patient.

The barcode printer 216 print out two barcode labels for the patient, one for the front of the patient chart and the other to be placed on the patient "flow sheet" (which is equivalent to the "check sheet" described above). This enables the system to later verify that the patient chart and the flow sheet always belong to the same patient.

The laser printer 214 prints out labels for the drug syringes used in the chemotherapy process. A nurse indicates how many treatments are planned for the patient and printer 214 prints out the complete set of labels for all treatments for this patient. Pre-printed labels are then placed inside the patient chart. In this regard, one label is used for each treatment session as the chemotherapy drug is prepared and placed into the syringe for the patient. The printed label includes the patient name and, in a preferred embodiment, a barcode as well so as to allow the system to later verify the patient chart, flow sheet, and syringes all are for the same patient just prior to treatment delivery.

Turning now to FIGS. 9(1) to 9(d), in a first step (block 220), the patient arrives for treatment. Although the next step (block 222) may have been done hours earlier in the day, the patient chart is pulled and treatment information obtained. In the next step (block 224), the syringe filled with appropriate chemotherapy drug and the pre-printed label described above is placed on the syringe.

As a next step (block 226), the patient is taken to a treatment room.

In the patient room, the nurse enters treatment room with patient chart (block 228) and scans chart barcode (block 230) and flow sheet barcode (block 232). The patient specific audio signal is generated at, in this preferred embodiment, the left speaker 208 (block 234) thereby allowing the patient to verify that it is their chart. The system also verifies on the screen of computer 200 that the two barcodes correspond to each other, i.e., that the patient chart and flow sheet are for same patient. The actual sequence preferably provides that the nurse select a treatment chair or regime from the touch-screen monitor 202 and indicate that a new patient has arrived for treatment, followed by the two barcodes being scanned and the matching audio signal being generated. At this point, the system would then display the patient name to the nurse, thereby providing a visual verification of the patient name.

In the next step, indicated by block 238, the patient is hooked up to an IV and some pre-treatment drugs administered. These drugs are anti-nausea, dehydration and like drugs. In one implementation of this embodiment of the invention, these drugs are also barcoded as well and are scanned at a scanning station prior to delivery. This would aid in charge capture by providing all drugs that are delivered in connection with a procedure are scanned into the system.

In the next step (block 242), the pre-chemotherapy treatment is administered. The pre-treatment drugs are normally administered for approximately one hour. The nurse sets up a "timing bag" at the same time, which causes an alarm to go off when pre-treatment drug delivery is completed. To assist here, a countdown timer is advantageously provided so as to enable the nurse to get an overview of each patient, their treatment status ("pre-chemo" or "chemo"), and the time remaining. After hanging the timing bag, the nurse would just select the appropriate patient chair on the touchscreen 202 and start a countdown timer to provide an alert as well as an indication as to when the pre-treatment is completed. As indicated by block 244, the nurse would normally leave the room during this period.

Figure 9A:
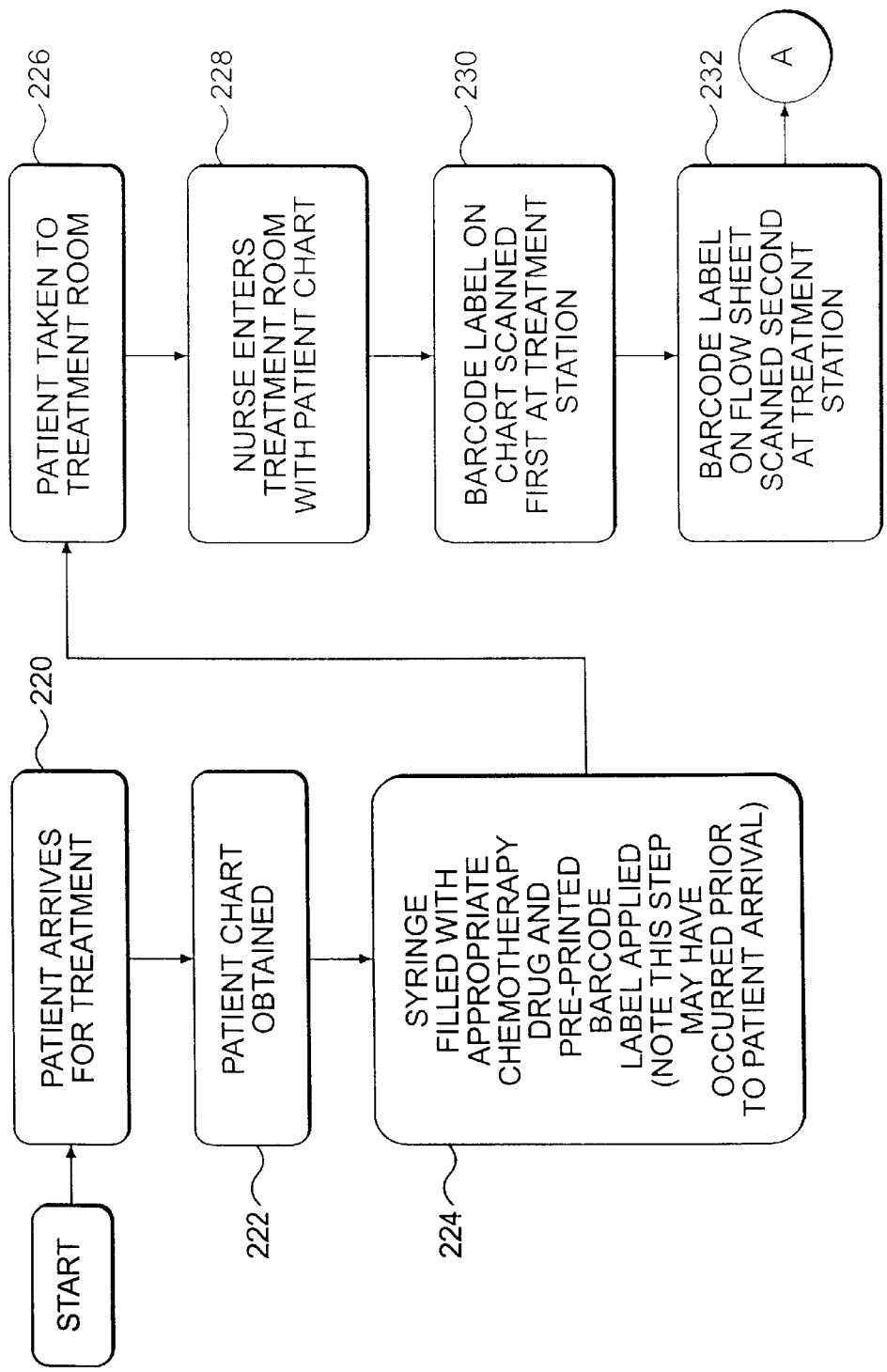
FIGS. 9(a) to 9(d) are, taken together, a block form flow chart of a chemotherapy treatment method in accordance with an additional embodiment of the invention.
Figure 9B:
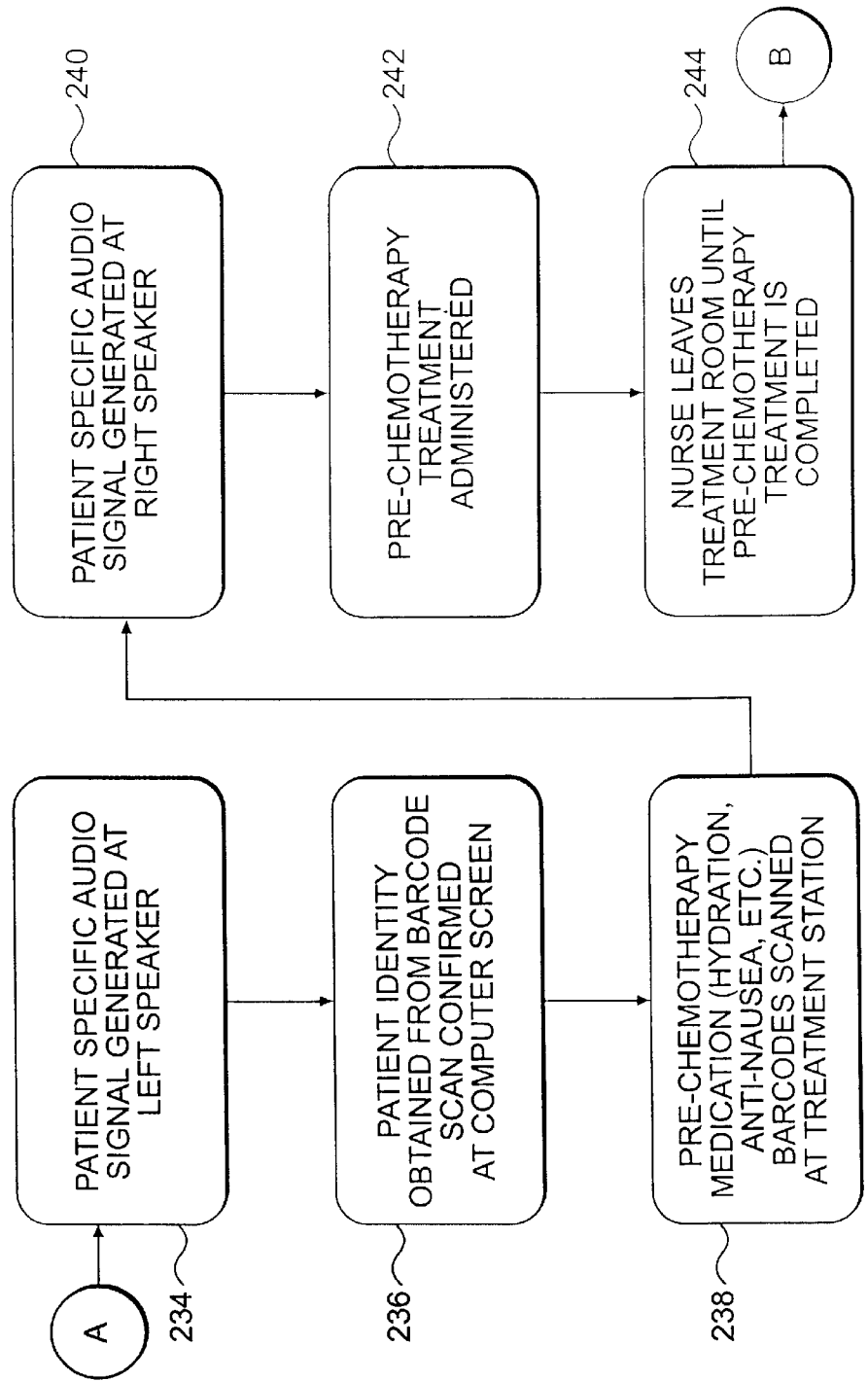
Figure 9C:
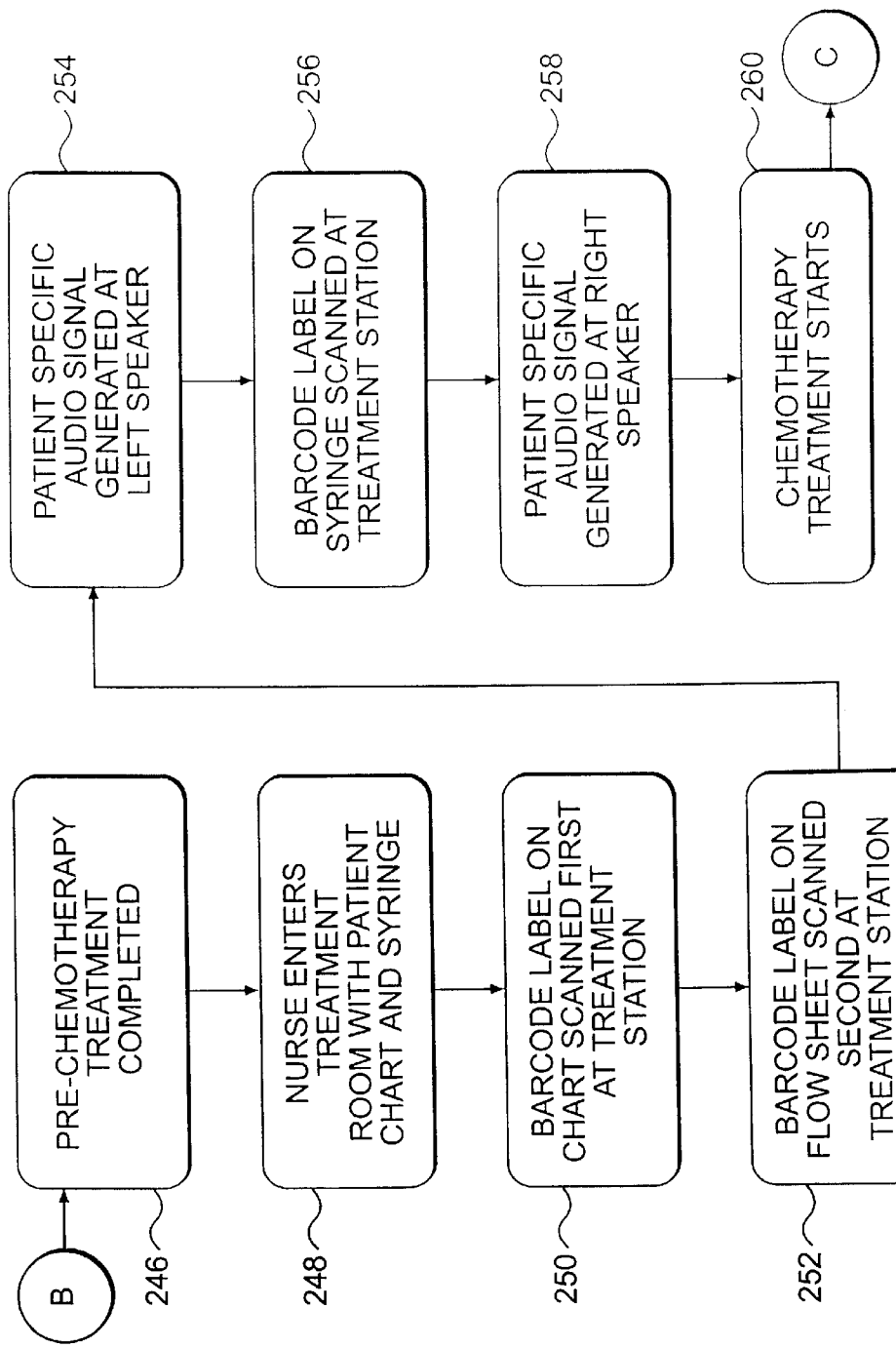
Figure 9D:
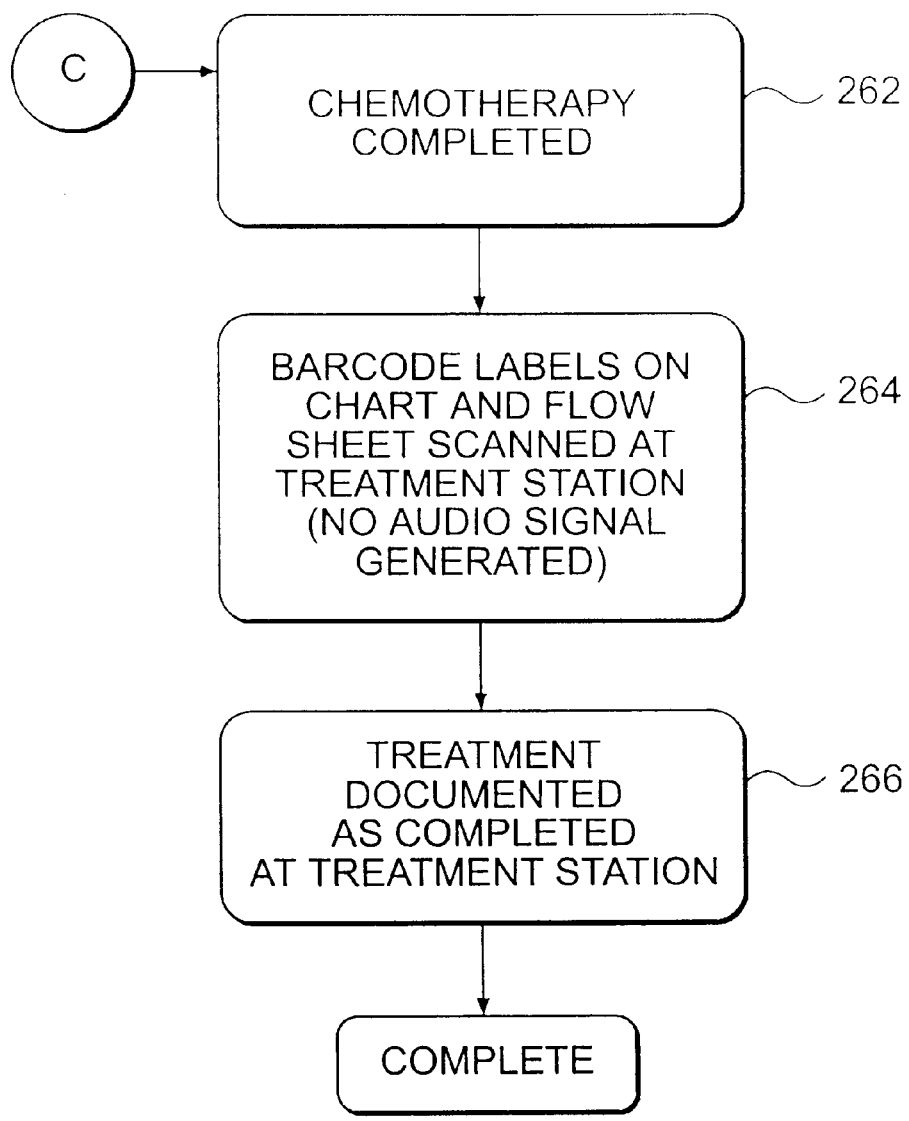

As set forth above, when pre-treatment is complete an alarm goes off. The nurse then retrieves patient pre-filled syringe and enters treatment room again with the patient chart (block 248). The patient chart, flow sheet, and syringe are scanned by scanner 212 and the patient specific audio signal is generated in response. More specifically, as indicated in FIG. 9(c), the barcode label on the patient chart is scanned first (block 250), the barcode label on the flow sheet is then scanned (block 252), and the patient specific audio signal is generated at the left speaker (block 254). The barcode label on the syringe is then scanned (block 256) and a patient specific tone generated at the right speaker (block 258) thereby enabling patient verification. This also verifies that all barcodes are assigned to the same patient and this, of course, includes the syringes. For high-risk patients (those with specific ICD-9 diagnosis or those flagged manually by the nurse during patient registration), the system also provides a prompt for a verification nurse to enter his or her badge or other identifier or initials at the station to indicate that someone has verified the drugs prior to administering the treatment. This simply adds an additional cross-check for high risk situations.

At this time, the nurse is able to start a countdown timer if desired for treatment delivery and the chemotherapy starts (step 260).

Once treatment is completed (block 262), the nurse selects a patient chair on touch-screen 202 and indicates that the treatment is completed. As indicated by block 264, the barcode labels on the patient chart and the flow sheet are scanned by scanner 212 but no audio signal is generated as this is not required for this step. A report can be generated at this time and printed in real-time to indicate the actual treatment given as well as the previous treatment history and the treatments remaining for the particular patient (block 266).

It will be appreciated from the foregoing that reports can be generated from the computer station indicating the particular patients that have been treated during a given time frame. The billing secretary can use this to verify that all patients treated for a given day were billed appropriately. In addition, in a preferred implementation, billing information is transferred electronically in real-time following treatment completion to a commercial medical billing software system across a network. This latter approach captures all chemotherapy charges electronically as they occur without requiring manual efforts alone, to track all of the billing.

It will be appreciated that all of the steps outlined above in connection with FIGS. 9(a) to 9(d) are not new and although a number of advantages of the invention should be apparent from the foregoing, it is believed to be helpful to contrast the treatment of FIGS. 9(a) to 9(d) with typical current treatment practice.

In a typical chemotherapy treatment, one nurse hand labels blank peel-off labels, and a schedule and chart are used to mix the required drugs. After the drugs are mixed, the syringe to be used is labeled with the patient name and the name of the drug (e.g., Adriamycin). The labeled syringe is placed next to the chemotherapy hood. The patient is next escorted into the infusion area and seated in the chair. Vital signs are taken and they are typically recorded on a blank scrap of paper for later transfer to the flow sheet of the patient's chart. The drugs (e.g., Zofran and Decadron) are started and during this period the nurse transfers the vital signs from the scrap of paper to the flow sheet. The "timing" bag drips in so as to delay the alarm referred to above and the infusion pump sounds the alarm when the bag runs out, indicating that it is time for the chemotherapy treatment to begin. At this point, the nurse hears the alarm and injects the syringe into the bag. The nurse uses then writes the drug name on the bag in "Sharpie" indelible marker, the bag is hung and the infusion rate is programmed into the pump. After the patient receives the infusion, the nurse or nurses must document the charges manually on several forms.

In the treatment method of the invention, the patient chart is used to mix the drugs and, as indicated previously, the registration process results in the printing of two barcodes, one for the chart and one for the flow sheet as well as the correct number of peel-off labels for the particular drug course or protocol. As set forth above, after the drugs are mixed, the syringe is labeled with a barcode label which includes the patient name, the name of the drug, etc. (e.g., "Jane Smith, Adriamycin, cycle 2 of 4" or "Jane Smith, Cytoxan, cycle 2 of 4").

The next part of the procedure is the same as in conventional treatment through the seating of the patient in the treatment chair. At this point, the front cover of the patient chart would be scanned and the audio signal generated in the left speaker. The chart is then opened, the flow sheet scanned and the audio signal generated in the right speaker. The vital signals are then taken and recorded in the chart on the flow sheet, in real time.

As in the currently used procedure, the drugs are then started and the "timing" bag infuses to delay the alarm, the infusion pump sounds when the bag runs out and the nurse hears the alarm indicating that it is time for chemotherapy to start. At this point, the nurse injects the previously labeled syringe or syringes into the bag which is labeled with a "Sharpie" marker as in the conventional process. At the end of the treatment, the nurse scans the patient chart and flow sheet and the above-mentioned billing prompt is generated (e.g., Bill patient? (Mrs. Jane Doe) yes/no). A positive response to the billing prompt generates a hardcopy sheet which is initialed by the nurse, signifying that the sheet agrees with the flow sheet and the signed hardcopy sheet is sent to billing.

In accordance with a further aspect of the invention, a medical billing system and method are provided which is specifically designed to ensure capture of charges that are sometimes missed or overlooked in billing for medical services. The system provides for logging in of the presence of a patient treatment chart or check sheet at a particular location such as a treatment room. The presence of the chart at that location can be determined, for example, based on an event involving the chart such as scanning of the chart by a scanning device at that location, as described above, or by using a tracking system which keeps track of the location of the document. When the patient treatment chart is determined to be located in the treatment room, the presumption is that the patient is being treated and thus that services are being rendered that should be billed for. By logging the presence of the chart at the treatment room into the billing system, the system is alerted to the fact that treatment has occurred or will occur and that a bill for the treatment should be generated. If no bill is generated, the billing system is queried as to why, and an inquiry is made.

Although the invention has been described above in connection with generating a characteristic audio signal in response to a match with an identifier, and this has important specific advantages, in an alternative embodiment, a visible indication or signal could be provided in a match situation, e.g., by energizing a light source. Further, a particular visual pattern unique to the patient and known to him or her could be generated in a match situation.

Turning to a more general consideration of the invention, it should be appreciated from the foregoing that the core method or process of the invention is not a primary verification tool. The invention serves to provide a secondary verification opportunity or documentation affirmation of other verification processes and does not replace or undermine other existing verification methods. One key difference between the invention and other systems or methods is that the invention enlists the patient in the identification process in a positive way. The enlistment is done in an aesthetically pleasing manner, with the above-described tones being emitted from the background. In this regard, it is noted that foreground stimuli would only further distract the caregiver and/or patient who is already bombarded by stimuli from numerous automated systems. Further, the invention does not contribute to automation induced user complacency because the identifying tone employed in the preferred embodiments of the invention, is a pleasing sound that differs from the beeps and alarms associated with other medical technologies which are designed on management by exception strategies. The system awards the user for doing the right thing, rather than penalizing the user for a misstep, which is how other systems work, and all this in view of the patient. Moreover, the tone is intended to provide specific reassurance, not alarm, in the listener. The invention preferably uses a database of protected audio files that produce a tone sequence specifically assigned to the individual patient. The listener then recognizes his or her tone chord on a long-term basis.

As more therapies move in the direction of chronic condition management as opposed to acute care management, the advantages of the invention will become even more apparent. This is particularly true in an environment noted for severe shortages in nursing personnel as well as in the area of high technology specialties such as radiation therapy, where new or temporary personnel are brought in to care for clients and patients with complicated chronic medical conditions. Delivering incorrect medication or treatments in highly specialized care settings can have a far more serious consequence in the medical environment of today than it would have just a few years ago. As treatments become much more tailored to an individual's disease or predisposition to a disease, the consequences of delivering even one wrong treatment may be far more toxic to the patient. Specific, targeted treatments often have a narrower therapeutic window, and may be beneficial only when delivered to a certain patient under certain conditions. The invention is flexible enough to be able to emit confirmatory tones under these refined scenarios, i.e., to confirm that the patient is the correct patient, the treatment chart is the right chart, and the sequencing or timing of the treatment is correct, and, as indicated above, this is all done in the background through the use of pleasant audio signals which can be recognized internationally, independently of language differences. It is noted that the chord sequences selected for international distribution could be derived from major chords for individuals of western background or a western country of origin, but could also be matched to the country of origin by using in the tone assignments, minor chords or other culturally more familiar chord-based tone sequences for individuals from non-western backgrounds or countries of origin. Further, a pre-chord sequence preferably provided that would serves as the geographic/year of origination of the tone assignment.

In some of the preferred embodiments of the invention described herein, two speakers are provided in the treatment room on opposite sides thereof. It has been found that "panning" of the audio signal across the room, i.e., playing the sound on one side of the room in response to a first scan and then playing the sound of the other side of the room in response to a second scan is advantageous. In this regard, panning helps with recognition of the audio match event, by differentiating the event from other sounds in the treatment room and by differentiating a repeat scan of the photo from scanning of the photo and then the check sheet. Preferably, the length of the tone chord is 2 to 3 seconds for a monosound setup and ½ to 2 seconds for the panning embodiments. These times are designed to provide the most efficient way to match task-critical entries in the shortest time and are based on maximizing discrimination based on tone contour and melody recognition.

It will be understood that a safety system ideally should be designed so that a successful recovery procedure can be implemented if the primary process should fail. The present invention does this because the invention serves to provide positive confirmation. In this regard, in a preferred embodiment, if the scanned patient or treatment demographics do not match, resulting in no tone sequence generation, the user hears nothing. The absence of the confirmatory tone sequence is what prompts the caregiver or patient to question the treatment that is about to be delivered. This is an important point because if the system of the invention should fail for any reason, the patient or caregiver is prompted by the absence of an audio confirmation to investigate further. The system of the invention is not an alarm that prompts the user to investigate because if the alarm should fail, the user does not know that the safety mechanism has failed. If the system is silent when a tone is expected, the user becomes more vigilant.

Although the invention has been described above in relation to preferred embodiments thereof, it will be understood by those skilled in the art that variations and modifications can be effected in these preferred embodiments without departing from the scope and spirit of the invention.

What is claimed:

1. A patient treatment check sheet containing at least a first field for entry of at least a name of a patient to be treated and a second field including printed patient treatment parameters and blanks to be filled in during a course of treatment of the patient, said check sheet further comprising at least one fixed patient identifier including characteristic coding adapted to be scanned by a scanning device to provide reading thereof and at least one removable patient identifier including said characteristic coding and adapted to be affixed to a further element to be used in the treatment of the patient, said at least one fixed patient identifier further comprising a first human readable identification symbol and said at least one removable patient identifier further comprising a second human readable identification symbol different from said first human readable identification symbol.

2. A patient treatment check sheet according to claim 1 wherein said further element is patient identification member selected from the group consisting of a patient photograph, a patient chart, a patient treatment verification sheet, a patient identification card, a patient identification band and a combination of a patient photograph and a patient chart.

3. A system as claimed in claim 1 wherein said at least one fixed patient identifier is located at a top portion of the check sheet and said at least one removable patient identifier is removably affixed in the check sheet at a bottom portion of the check sheet.

4. A verification system for use in verification of an identity of a patient about to undergo medical treatment administered to the patient in a treatment room under control of at least one medical practitioner, said system comprising:
- a verification workstation including electronic storing means for storing a patient identifier assigned to the patient to be treated;
- at least one scanning device for scanning a scannable patient identifier which uniquely identifies the patient to be treated; and
- means for generating a characteristic audible output assigned to the patient to be treated and unique to the patient, responsive to matching of the patient identifier scanned by said scanning device and the patient identifier stored by said electronic storing means at said verification workstation.

5. A system as claimed in claim 4 wherein the medical treatment comprises radiation therapy, and said system further comprises an accelerator for providing radiation therapy treatment, and an acceleration workstation including a monitor for controlling said accelerator, said verification workstation being linked to said accelerator workstation.

6. A system as claimed in claim 4 wherein said verification workstation includes both a barcode reader and a card swipe reader.

7. A system as claimed in claim 4 wherein said scannable patient identifier comprises a bar code carried by a treatment chart for the patient.

8. A system as claimed in claim 7 wherein said system includes first and second scanning devices, located at spaced locations within said treatment room, for separately scanning scannable patient identifiers carried, respectively, by (i) a treatment chart and (ii) at least one other element associated with the patient to be treated.

9. A system as claimed in claim 8 wherein the first and second scanning devices each comprise a barcode reader.

* * * * *